United States Patent [19]
Savage et al.

[11] Patent Number: 6,032,673
[45] Date of Patent: Mar. 7, 2000

[54] METHODS AND DEVICES FOR TISSUE REMOVAL

[75] Inventors: George M. Savage, Portola Valley; Donald L. Alden, Sunnyvale; Arnold J. Kresch, Portola Valley; Jeffrey J. Christian, San Jose, all of Calif.

[73] Assignee: FemRx, Inc., Sunnyvale, Calif.

[21] Appl. No.: 08/912,259

[22] Filed: Aug. 15, 1997

Related U.S. Application Data

[63] Continuation-in-part of application No. 08/322,680, Oct. 13, 1994, abandoned, and a continuation-in-part of application No. 08/542,289, Oct. 12, 1995, abandoned, and a continuation-in-part of application No. 08/559,969, Nov. 17, 1995, abandoned, and a continuation-in-part of application No. 08/732,044, Oct. 16, 1996, abandoned, and a continuation-in-part of application No. 08/705,228, Aug. 29, 1996, abandoned, and a continuation-in-part of application No. 08/705,229, Aug. 29, 1996, abandoned, and a continuation-in-part of application No. 08/596,626, Dec. 8, 1995, and a continuation-in-part of application No. PCT/US96/17454, Nov. 1, 1996.

[60] Provisional application No. 60/013,637, Mar. 18, 1996, provisional application No. 60/006,325, Nov. 7, 1995, and provisional application No. 60/008,226, Nov. 8, 1995.

[51] Int. Cl.[7] ............................................. A61B 17/39
[52] U.S. Cl. .............................. 128/898; 606/46; 606/41
[58] Field of Search ......................... 606/41, 42, 45–50; 128/898; 604/21, 22; 600/105, 135

[56] References Cited

U.S. PATENT DOCUMENTS

| | | |
|---|---|---|
| 1,127,948 | 2/1915 | Wappler . |
| 1,303,135 | 5/1919 | Wappler . |
| 1,930,214 | 10/1933 | Wappler . |
| 2,012,363 | 8/1935 | Vogel . |
| 2,484,059 | 10/1949 | Wallace . |
| 2,815,757 | 12/1957 | Piar . |
| 3,147,749 | 9/1964 | Marsh . |
| 3,850,162 | 11/1974 | Iglesias . |
| 3,850,175 | 11/1974 | Iglesias .................................. 606/46 |
| 3,939,839 | 2/1976 | Curtiss . |
| 3,942,530 | 3/1976 | Northeved . |
| 3,945,375 | 3/1976 | Banko . |
| 4,132,227 | 1/1979 | Ibe . |
| 4,134,406 | 1/1979 | Iglesias . |
| 4,149,538 | 4/1979 | Mrava et al. . |
| 4,190,051 | 2/1980 | Iglesias . |
| 4,362,160 | 12/1982 | Hiltebrandt . |
| 4,559,943 | 12/1985 | Bowers .................................. 606/37 |
| 4,607,621 | 8/1986 | Wheeler . |

(List continued on next page.)

FOREIGN PATENT DOCUMENTS

| | | |
|---|---|---|
| 0 287 368 | 10/1988 | European Pat. Off. . |
| 502 607 | 3/1939 | United Kingdom . |
| WO 93/08738 | 5/1993 | WIPO . |

OTHER PUBLICATIONS

Product Brochure from Richard Wolf Medical Instruments Corporation entitled, "Hysteroresectoscope System for Endometrial Ablation," 5th World Congress on Transvaginal Sonography, FL, May 7–10, 1992.

*Primary Examiner*—Michael Peffley
*Attorney, Agent, or Firm*—Verne E. Kreger

[57] ABSTRACT

The present invention provides a tissue resection device comprising a handle housing having a fluid infusion lumen. A shaft is reciprocatably mounted to the housing, the shaft having an aperture adjacent to a distal end and a fluid and tissue aspiration lumen extending from the aperture to a proximal end of the shaft. A cutting member is disposed adjacent to the aperture to sever tissue as the shaft is reciprocated, and an imaging mechanism on the housing is oriented toward the cutting member, thereby allowing the attending surgeon to optically direct the removal of body cavity tissue. A chopping mechanism is disposed within the lumen of the shaft to reduce the size of tissues passing through the lumen.

24 Claims, 33 Drawing Sheets

U.S. PATENT DOCUMENTS

| | | |
|---|---|---|
| 4,679,558 | 7/1987 | Kensey et al. . |
| 4,681,106 | 7/1987 | Kensey et al. . |
| 4,756,309 | 7/1988 | Sachse et al. . |
| 4,815,462 | 3/1989 | Clark . |
| 4,821,731 | 4/1989 | Martinelli et al. . |
| 4,834,729 | 5/1989 | Sjostrom . |
| 4,842,578 | 6/1989 | Johnson et al. . |
| 4,917,082 | 4/1990 | Grossi et al. . |
| 4,936,281 | 6/1990 | Stasz . |
| 4,986,825 | 1/1991 | Bays et al. . |
| 4,998,527 | 3/1991 | Meyer . |
| 5,000,185 | 3/1991 | Yock . |
| 5,019,036 | 5/1991 | Stahl . |
| 5,092,872 | 3/1992 | Segalowitz . |
| 5,133,713 | 7/1992 | Huang et al. . |
| 5,169,397 | 12/1992 | Sakahita et al. . |
| 5,170,805 | 12/1992 | Kensey et al. . |
| 5,176,677 | 1/1993 | Wuchinich . |
| 5,196,011 | 3/1993 | Korth et al. . |
| 5,199,437 | 4/1993 | Langberg . |
| 5,201,731 | 4/1993 | Hakky . |
| 5,267,998 | 12/1993 | Hagen . |
| 5,269,780 | 12/1993 | Roos . |
| 5,277,696 | 1/1994 | Hagen ................................ 606/41 |
| 5,295,990 | 3/1994 | Levin . |
| 5,304,124 | 4/1994 | Essig et al. . |
| 5,312,399 | 5/1994 | Hakky et al. . |
| 5,313,949 | 5/1994 | Yock . |
| 5,314,438 | 5/1994 | Shturman . |
| 5,325,860 | 7/1994 | Seward et al. . |
| 5,335,663 | 8/1994 | Oakley et al. . |
| 5,351,692 | 10/1994 | Dow et al. . |
| 5,354,296 | 10/1994 | Turkel . |
| 5,364,395 | 11/1994 | West, Jr. . |
| 5,373,846 | 12/1994 | Widder . |
| 5,391,197 | 2/1995 | Burdette et al. . |
| 5,395,363 | 3/1995 | Billings et al. . |
| 5,441,503 | 8/1995 | Considine et al. ................ 606/46 |
| 5,443,470 | 8/1995 | Stern et al. . |
| 5,445,638 | 8/1995 | Rydell et al. . |
| 5,456,689 | 10/1995 | Kresch et al. . |
| 5,549,605 | 8/1996 | Hahnen . |
| 5,569,244 | 10/1996 | Hahnen . |
| 5,582,610 | 12/1996 | Grossi et al. ..................... 606/46 |
| 5,599,349 | 2/1997 | D'Amelio . |
| 5,634,924 | 6/1997 | Turkel et al. . |
| 5,658,280 | 8/1997 | Issa . |
| 5,669,906 | 9/1997 | Grossi et al. . |
| 5,681,262 | 10/1997 | Isse ................................... 600/127 |
| 5,697,281 | 12/1997 | Eggers et al. . |
| 5,697,536 | 12/1997 | Eggers et al. . |
| 5,697,882 | 12/1997 | Eggers et al. . |
| 5,697,909 | 12/1997 | Eggers et al. . |
| 5,709,679 | 1/1998 | Essig et al. ....................... 606/46 |

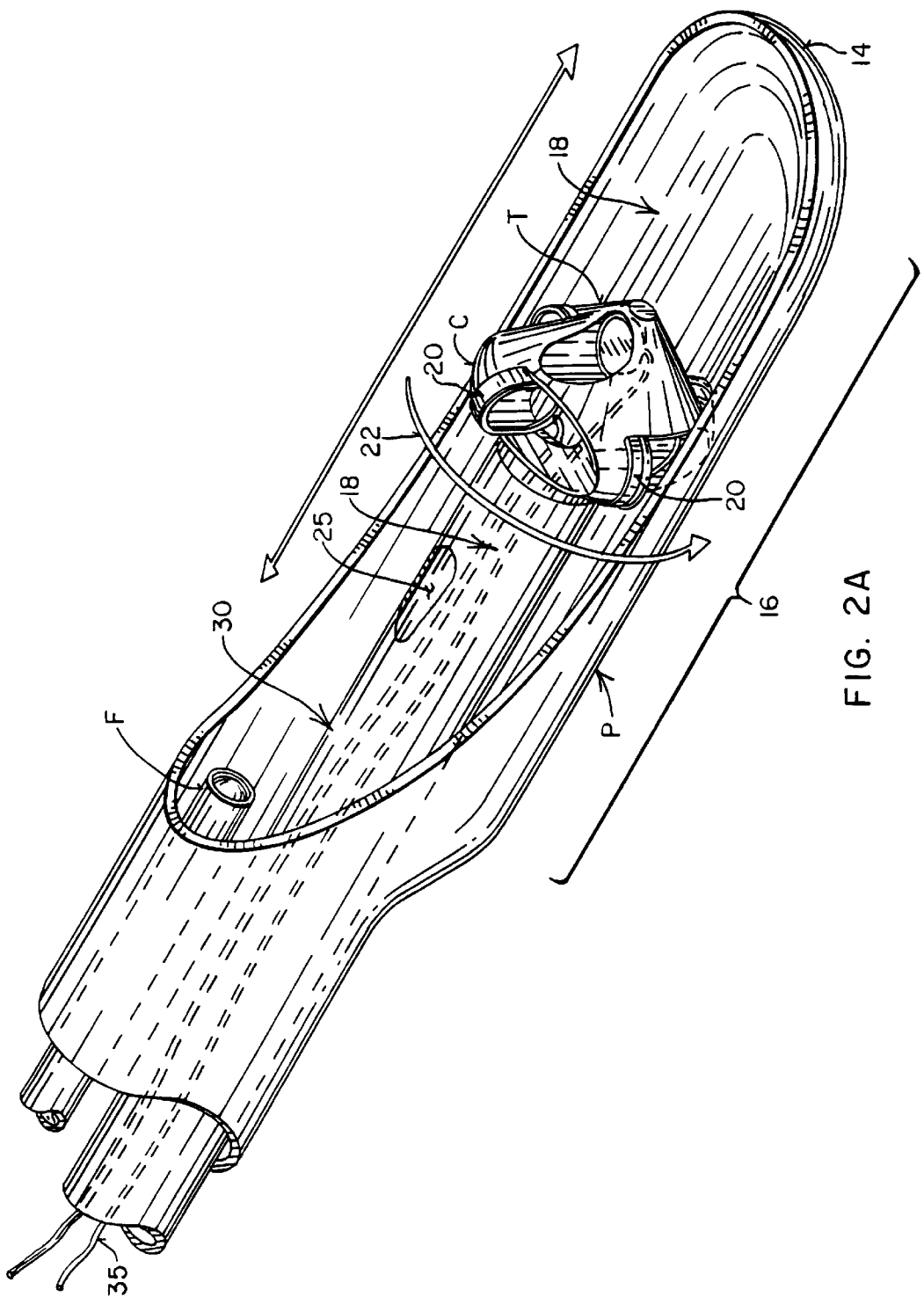

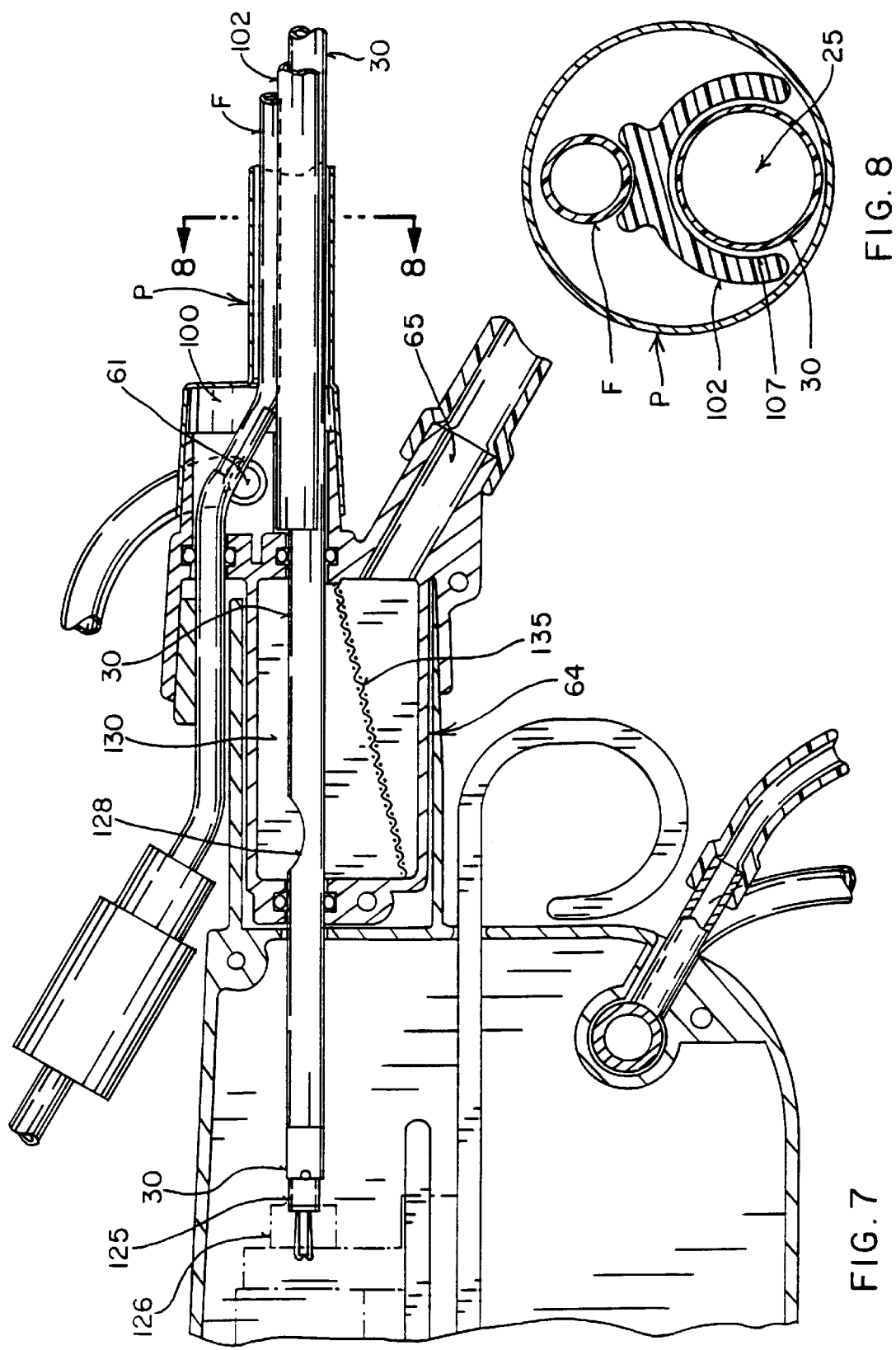

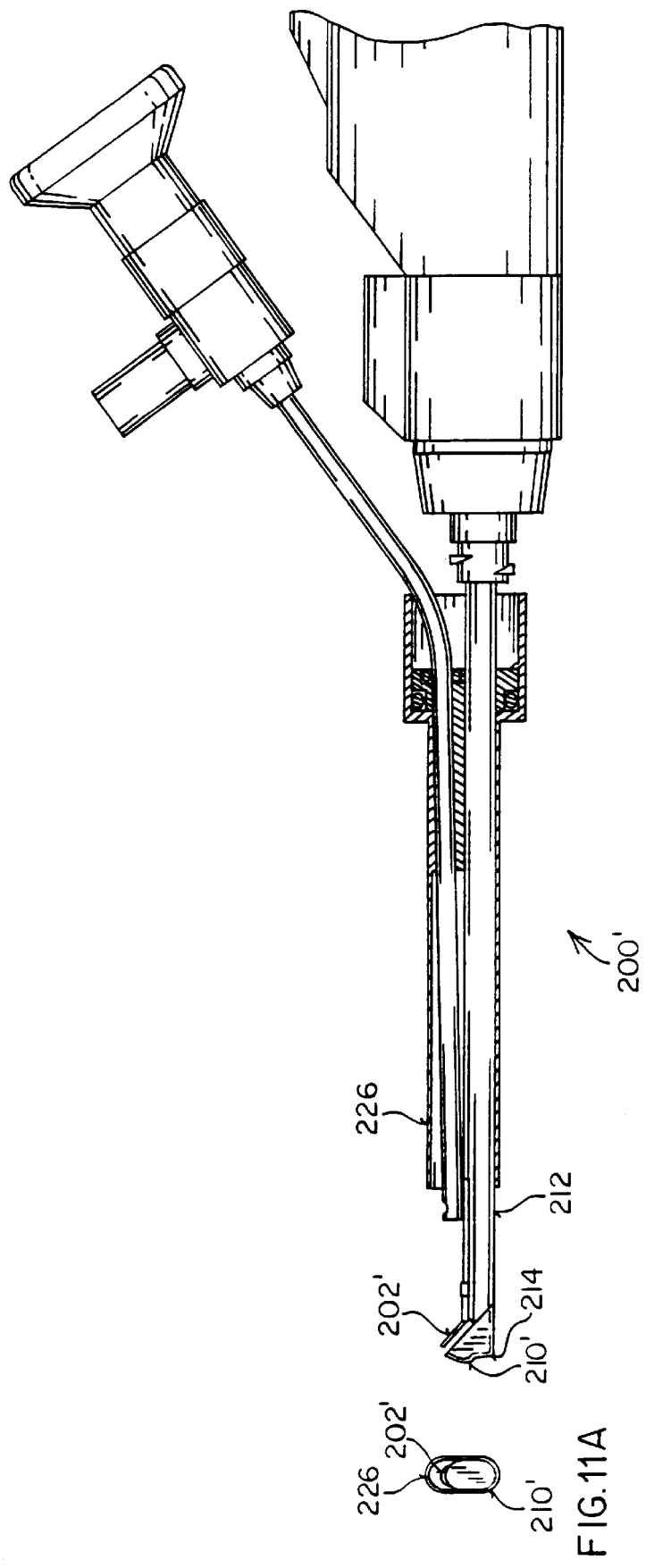

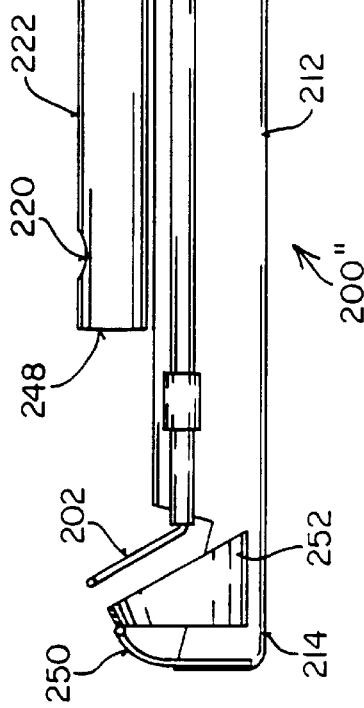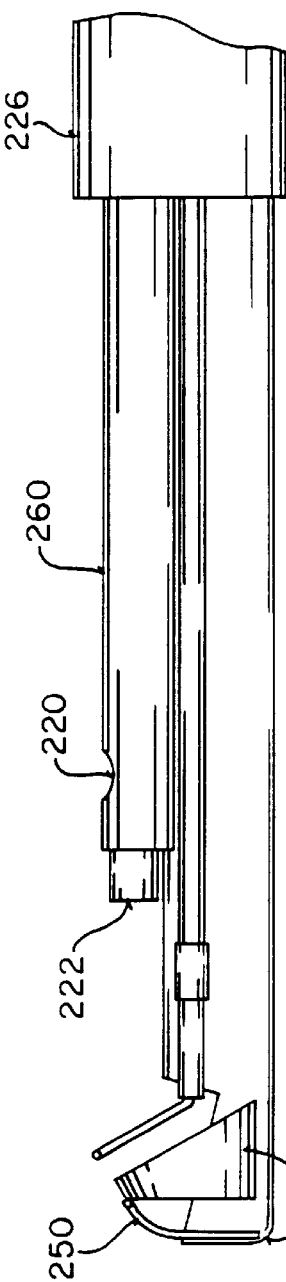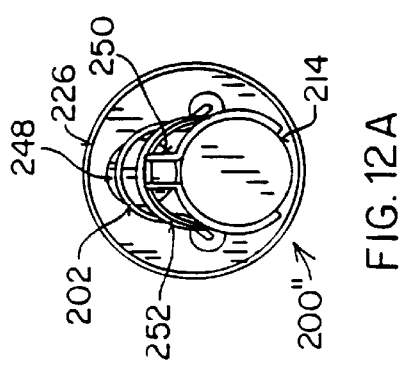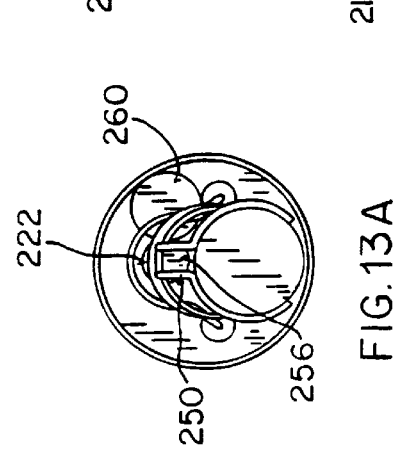

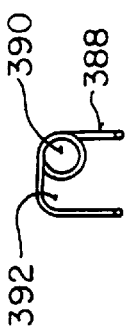
FIG. 21A
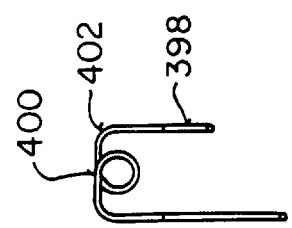
FIG. 21B
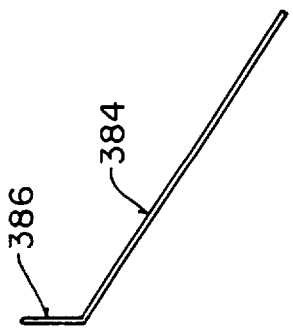
FIG. 20A
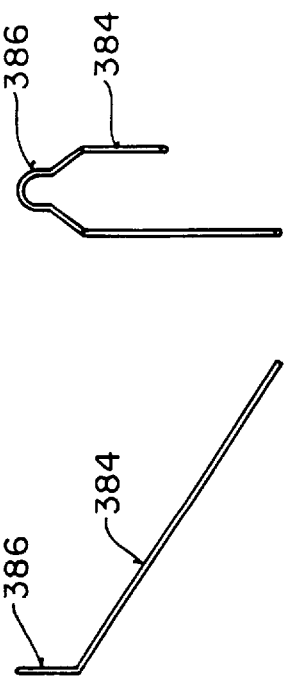
FIG. 20B
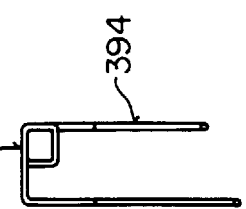
FIG. 23A
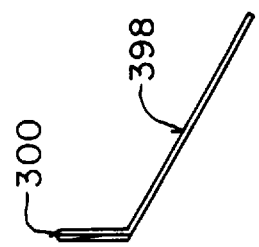
FIG. 23B
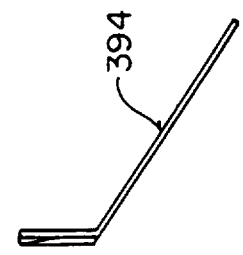
FIG. 22A
FIG. 22B

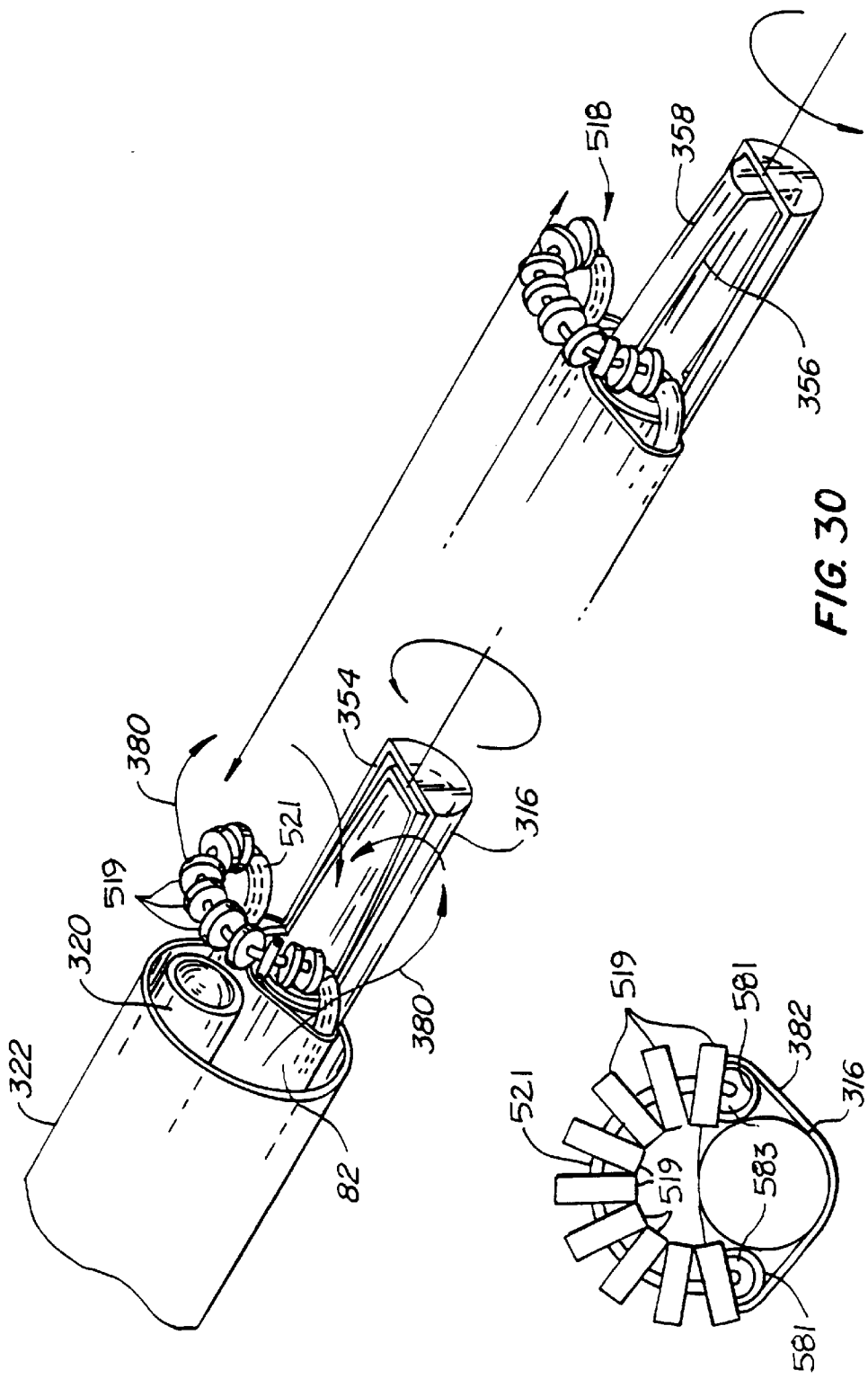

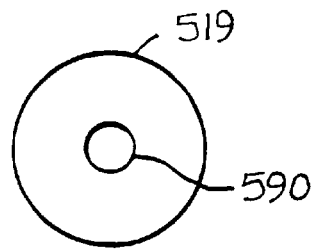
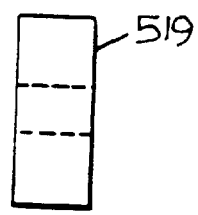
FIG. 32A      FIG. 32B
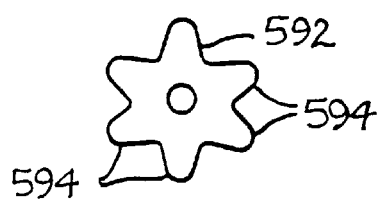
FIG. 33
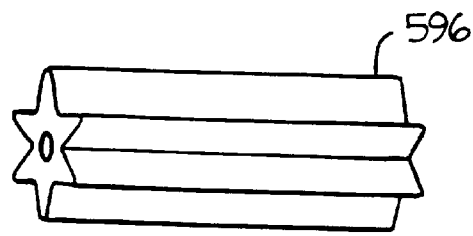
FIG. 33A
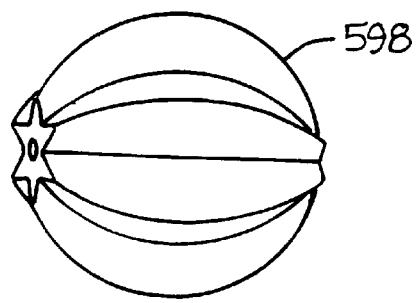
FIG. 33B

METHODS AND DEVICES FOR TISSUE REMOVAL

CROSS-REFERENCE TO RELATED APPLICATIONS

This application is a continuation-in-part and claims priority from U.S. patent application Ser. Nos. 08/322,680, filed Oct. 13, 1994 (now abandoned); Ser. No. 08/542,289, filed Oct. 12, 1995 (now abandoned); Ser. No. 08/559,969, filed Nov. 17, 1995 (now abandoned); Provisional Ser. No. 60/013,637, filed Mar. 18, 1996; Ser. No. 08/732,044, filed Oct. 16, 1996 (now abandoned); Provisional Ser. No. 60/006,325, filed Nov. 7, 1995; Ser. No. 08/705,228, filed Aug. 29, 1996 (now abandoned). Provisional Ser. No. 60/008,226, filed Nov. 8, 1995; Ser. No. 08/705,229, filed Aug. 29, 1996 (now abandoned); Ser. No. 08/596,626, filed Dec. 8, 1995; and International PCT patent application Ser. No. PCT/US96/17454, filed Nov. 1, 1996; the full disclosures of which are incorporated herein by reference.

BACKGROUND OF THE INVENTION

This invention relates to a method and device for tissue removal, especially for surgical treatment of the uterus or prostate.

Electrocautery has been in use for many years as a general surgical tool, such as for trans-cervical fibroid removal. The uterus is first flooded under pressure with a nonconductive fluid, such as sorbitol-mannitol fluid or the like under sufficient pressure to separate the walls of the uterus and render the surgical site suitable for optical fiber observation. This procedure is generally described as uterine cavity distension. During this flooding, an electrocautery surgical tool is inserted into the uterus through the cervix. Electrical current at high voltage settings (typically an alternating current about 750 KHz and 2000–9000 volts) is transmitted from a cutting surface of the surgical instrument to the surgical site. The cutting surface usually consists of a wire or solid shape. The transmission of current to the uterus is monopolar, and the circuit is completed by a conductive path to the power unit through a conductive pad applied to the patient's skin.

The electrical current is concentrated at the cutting surface. Heat generated from the resistance of tissue to the flow of electrical current is high enough to vaporize cells near the cutting surface. Thus, a cut is made with very little physical resistance to the cutting motion. Heat from the cut cauterizes small blood vessels so that visibility and control remain good.

During uterine cavity distension, the same electrical resistance heating may be used at lower power settings to cauterize bleeding tissue and to kill selected areas of the tissue through ablation. Such cautery electrodes can be larger in area so as to treat broader surfaces. Cautery is used in gynecology to ablate the endometrial lining of the uterus. This procedure is often performed using a conductive roller similar in shape to a football which heats a wide swath of tissue along the inner surface of the uterus.

Electrocautery tools are compact and require a minimum of area in which to work. Since the tool only cuts when the power is turned on, it can be safely maneuvered into small areas. Electrocautery has found broad general application in the treatment of enlarged prostate glands and in the removal of uterine fibroids.

A secondary effect of the removal of tissue, particularly in the areas of prostate reduction and fibroid removal, is that separated tissue fragments typically remain in the working area and must be periodically flushed or suctioned away to preserve the required visibility necessary for surgery. The clean, well-controlled action of electrocautery is now slowed by this need to remove fragments which obstruct visibility. Therefore, the requirement for intermittent clearing of the surgical site prolongs fibroid removal and other electrosurgical procedures.

It is known that ultrasound can add significant value to tissue resection and ablation procedures. Using high-frequency ultrasound, anatomical landmarks and tissue features can be imaged in depth, which cannot be done by optical instruments. Depth information provides improved guidance and monitoring capabilities. It enables the surgeon to monitor the progress of tissue treatment, and thereby lessens the risk of complications. In addition, the improved visualization provided by ultrasound can help to shorten procedure times.

At the present time as for example during uterine cavity distention, it is not practical to introduce ultrasound probes without considerable complication.

To perform ultrasound measurements during electrocautery, the surgical probes for the electrocautery procedure must first be removed and thereafter, ultrasound introduced. Finally, and after such measurements, surgery can resume with reintroduction of the surgical probes. With such procedures, the surgeon has difficulty returning to the original surgical site. For this reason, ultrasound is not usually utilized for measurement of uterine wall thickness by an intrauterine transducer.

SUMMARY OF THE INVENTION

A tissue removal device for preferred use in an organ inflated with substantially non-conductive optically transparent fluid under pressure is disclosed. In most embodiments, the instrument includes a rigid shaft having a proximal end, a distal end, and defining a perfusion lumen extending therebetween. At the distal end of the shaft, the shaft is provided with a rounded blunt end having an elongate aperture exposing the lumen near the distal end. A removable drive tube is rotatably disposed within the shaft lumen and has a proximal end, a distal end, and a drive tube aspiration lumen extending therebetween. A cutting head is mounted on the distal end of the drive tube and has a laterally disposed cutting edge which can resect either by conventional cutting or electrocautery. This laterally disposed cutting edge is communicated to an internal passage between the cutting edge and the aspiration lumen of the drive tube so that tissue severed as the cutting head is rotated may be drawn directly into the aspiration lumen. A housing is attached to the proximal end of the shaft.

Preferably, a DC motor in the housing is connected to rotate the drive tube and thus the laterally disposed cutting head. Connection is provided on the housing for connecting the perfusion shaft lumen to a perfusion source and the aspiration lumen to an aspiration source. Preferably, an optic fiber or hysteroscope at the proximal end of the elongate aperture of the shaft provides illumination and an optical view of surgery while a distally mounted and laterally exposed ultrasound transducer is disposed with a solid angle of interrogation including the surgical site. The surgical instrument finds preferred use in the uterus during uterine cavity distention where surgery occurs at the cutting head and can be disposable. During the surgical process, the cutting head is preferably drawn distally of the elongate cutting aperture towards the viewing optical fiber with the ultrasound transducer positioned to acoustically interrogate the operative site immediately after surgery.

A novel feature of this design is that the morsels removed by the cutter are extracted immediately through the aspiration lumen in the rotating shaft. Controlling the size of the chips, and directing them into the shaft center is achieved through the design of the cutter head. Controlled aspiration, typically by a finger actuated valve, occurs from within the cutter head to a retain sieve. Vision of the surgical site is improved.

Another novel feature of this design is a removable and disposable cartridge which surrounds the rotating cutter shaft where it enters the handle, and filters the surgical debris from the sorbitol-mannitol fluid used in the uterine cavity during the procedure for distention and visualization. The removed tissue is contained in the cartridge which can be sent intact to a laboratory for examination.

A feature of this design is that the handle, external shaft, and motor assembly can be re-used allowing for cost savings. The cutter head and shaft are intended to be disposable and can quickly plug into the handle assembly.

Another feature of this design is that a variety of cutter head configurations can be built which will allow for greater flexibility and effectiveness in treatments. A few examples are: an end-effect cutter for removing tissue at the end of the cutter axis; a smooth, or textured, head for ablation of uterine lining; and a narrow cutter for trimming the edge of a feature, or for cutting into a restricted area. Another feature of this design is the control which is provided by the motorized operation. In conventional procedures, a surgeon is required to expend coordinated effort in moving and extracting debris in addition to actually making a series of cuts. With the motorized cutter and extraction system, the surgeon directs the cutter head to the area to be treated, and slowly draws the cutter through the fibroid to be removed. A trigger attached to the driving motor enables the cutting head to traverse the elongate aperture, preferably from the distal end to the proximal end toward the viewing fiber. Cutting is a matter of pressure and time at any particular area, and the feedback of the results is immediate through both visual observation and ultrasound interrogation in the wake of the resection. Fatigue is reduced, allowing for more precise work.

Another feature of this design is the ability to vary the motor speed and direction. Low speed cutting is more accurate and offers better control. Where a cutter head with electrocautery cutting edges is utilized, stopping or reversing the rotation offers the ability to treat the surface of an organ or to cauterize an area which is bleeding. Another feature of this design is the use of the journal bearing as an electrical contact for the high voltage cutting current. This eliminates the need for a large slip-ring assembly, making the handle more compact and less expensive.

Yet another feature of this design is the mounting of the probe to a base unit adapted for fitting to the hand of the surgeon. Typically, the body of the drive unit is grasped between the hand and thumb. The forefinger (trigger finger) is utilized to cause the cutting head to traverse the elongate aperture for cutting at the surgical site. Motion of the housing directs the distal end of the probe to the surgical site.

Another feature of this design is the incorporation of the aspiration control valve into the handle. The valve is positioned so that it can be operated with one finger while steadying the tool and controlling the motion of the cutter with the rest of the hand. Aspiration can be made as vision and surgery requires with infusion through the instrument maintaining require cavity pressure.

Another feature of this design is that the cutter head and shaft, and scope can be removed from the outer sheath to allow the use of an obturator for dilating the cervix and introducing the sheath.

An added advantage of this invention is the incorporation of a sound transducer to the cutting head. Such a transducer can measure remaining organ wall thickness, preferably immediately after surgery. Surgery can be conveniently limited to avoid damage to adjacent organs. The invention further provides an exemplary method for resecting tissue from a patient's internal body structure. According to the method, the depth of tissue to be resected is ultrasonically measured, and the tissue is removed from the internal body structure. In a preferable aspect, the removed tissue is chopped into smaller morsels which are then evacuated from the patient.

In one particular aspect of the method, the tissue is electrosurgically removed by translating an electrosurgical wire along and through the tissue. In this way, the tissue is removed in elongate strips which can then by chopped into smaller morsels by rotating a sharpened blade in the uterus. In another particular aspect, the internal body structure is optically visualized while removing the tissue. In still another aspect, bleeding tissue on the internal body structure is cauterized.

The invention provides another exemplary method for resecting tissue from a patient's internal body structure by directing an electrosurgical member into the tissue and translating the electrosurgical member through the tissue to electrosurgically remove tissue from the internal body structure. The removed tissue is then chopped into smaller morsels. Once the tissue is reduced in size, the morsels are evacuated from the patient. In a preferred aspect, the electrosurgical member is an electrosurgical wire which is translated to remove the tissue in elongate strips. Simultaneously, a sharpened blade is rotated in the internal body structure to chop the removed tissue into smaller morsels for evacuation.

In a particularly preferable aspect, the depth of tissue to be removed is measured by use of an ultrasonic transducer. In another aspect, the internal body structure is optically visualized. In a further aspect, bleeding tissue on the internal body structure is cauterized.

In yet another method of the invention, tissue is resected from a body structure by providing a probe having a proximal end, a distal end, a lumen extending therebetween, and an aperture exposing the lumen near the distal end. An electrosurgical wire is also provided near the distal end of the probe, and a drive member is rotatably disposed within the probe lumen. A rotatable cutting member is provided at the distal end of the drive member with the cutting member being accessible through the aperture. The probe is positioned at a surgical site near the body structure, and the electrosurgical wire is translated along tissue at the surgical site to resect tissue from the body structure. To chop the removed tissue into smaller morsels, the cutting member is rotated as the tissue is directed into the cutting member.

In one particular aspect, the morsels are aspirated from the body structure through the probe lumen. In another aspect, the depth of tissue resection is ultrasonically viewed. In still anther aspect, an electrically conductive element on the probe is provided with current, and the electrically conductive element is placed against bleeding tissue on the body structure to effect cauterization.

The invention provides an alternative embodiment of tissue resection device which includes an elongate body having a proximal end and a distal end. Means is provided near the distal end for electrosurgically removing tissue, and an ultrasonic transducer is disposed on the device for ultrasonically imaging tissue at a surgical site to determine depth of tissue to be resected. In a particularly preferable aspect, the ultrasonic transducer is held in an axially translatable shaft disposed adjacent the elongate body. In this way, translation of the shaft moves the transducer to a desired imaging site.

In one aspect, the elongate body includes a lumen extending between the proximal and the distal ends and an aperture exposing the lumen near the distal end. Means is provided for evacuating resected tissue through the lumen. To assist in the evacuation of tissue, means is provided in the lumen for chopping resected tissue into smaller morsels. Preferably, the chopping means includes a rotatable cutting member.

In yet another aspect, means for directing removed tissue to the chopping means is provided. Preferably, the directing means includes an extension on the distal end of the elongate body.

In still another aspect, an optical fiber is provided and includes a viewing end disposed near the wire. The optical fiber is preferably held in a translatable shaft adjacent the elongate member. In this way, cutting of tissue with the wire may be observed through the optical fiber. The directing means can also be provided with an aperture that is aligned with the viewing end of the optical fiber so that tissue beyond the distal end of the elongate body may be observed through the optical fiber. In one aspect, at least a portion of the directing means is electrically conductive so that electrocauterization of tissue can be effected upon contact with the directing means.

The invention provides yet a further alternative embodiment of a tissue resection device that includes an elongate body having a proximal end and a distal end. An electrosurgical wire is disposed near the distal end of the elongate body, and chopping means is disposed near the distal end of the elongate body for chopping resected tissue into smaller morsels. A housing is attached to the proximal end of the elongate body, and means is disposed in the housing for actuating the chopping means.

In a preferable aspect, an ultrasonic transducer is disposed near the wire for ultrasonically imaging depth of tissue resection at a surgical site. Preferably, the ultrasonic transducer is held in an axially translatable shaft disposed adjacent the elongate body so that translation of the shaft moves the transducer to a desired imaging site. In another aspect, means is provided for directing removed tissue to the chopping means. The directing means in one aspect preferably includes an extension on the distal end of the elongate body.

An optical fiber having a viewing end disposed near the wire can also be provided for observing the cutting of tissue or for positioning of the electrocautery wire. In one aspect, the directing means includes an aperture that is aligned with the viewing end of the optical fiber so that tissue beyond the distal end of the elongate body may be observed through the optical fiber.

In still another aspect, the elongate body includes a central lumen and an aperture exposing the lumen near the distal end of the elongate body. The chopping means, which preferably includes a rotatable cutting member, is disposed in the central lumen and is accessible through the aperture. Aspiration means is provided for aspirating the chopped tissue through the central lumen, and in a further aspect at least a portion of the directing means is electrically conductive so that electrocauterization of tissue can be effected upon contact with the directing means.

In one particular embodiment, the invention provides for a diagnostic device that can be used to diagnose abnormalities in the endometrial cavity or the uterine wall. Diagnosis is accomplished by mapping the uterus from within the endometrial cavity. According to this method, an ultrasonic transducer is introduced into the endometrial cavity. The transducer is then actuated at various positions within the endometrial cavity to measure the thickness of the uterine wall. The measurements are then processed to produce a map of the uterus. The map can then be evaluated to diagnose any abnormalities.

In a first aspect, the present invention provides a tissue resection device comprising a handle housing having a fluid infusion lumen. A shaft is reciprocatably mounted on the handle housing, the shaft having an aperture adjacent to a distal end and a fluid and tissue aspiration lumen extending from the aperture to a proximal end of the shaft. A cutting member is disposed adjacent to the aperture to sever tissue as the shaft is reciprocated, and an imaging mechanism on the handle housing is oriented toward the cutting member, thereby allowing the attending surgeon to optically direct the removal of body cavity tissue. A chopping mechanism disposed within the lumen of the shaft reduces the size of tissues passing through the lumen.

Typically, the cutting member produces strips of tissue, which the chopping mechanism shears into smaller, more easily aspirated tissue fragments as they enter the aperture. Preferably, the imaging mechanism is distally oriented, and the aperture is radially oriented and extends distally of the cutting member. This arrangement allows the removal of tissue strips in the proximal direction toward a fixed viewpoint, and directs the severed tissue into the aperture, thereby minimizing the danger that the probe will inadvertently cut to a greater depth than is intended, and greatly increasing the safety of the resection procedure. Furthermore, directing tissue with aspiration flow into the radially oriented aperture, rather than resorting to an axially oriented endcap, significantly increases cutting depth and decreases cutting drag.

Preferably, the handle housing comprises a sheath which is removably disposed over the shaft, the infusion lumen extending to a distal end of the sheath adjacent to the imaging mechanism. The sheath thus provides an irrigation flow path directed over the imaging mechanism and toward the cutting member. Such an irrigation flow path washes clean, clear irrigation fluid over the critical portion of the field of view of the resection procedure. Generally, the imaging mechanism comprises an optical lens and fiber-optic image guide, although ultrasound or other imaging modalities may be used in some embodiments.

In a particularly preferred embodiment, the tissue resection device of the present invention includes an electrically conductive distal surface disposed distally of the aperture. At least a portion of the electrically conductive surface is distally oriented.

In work done in connection with the present invention, it has been discovered that a resection probe having a reciprocatable cutting member benefits from an alternative mechanism for treating body cavity tissues having surfaces which are generally proximally oriented relative to the axis of the probe. The electrically conductive surface of the present invention allows ablation of such tissues by sweeping the distal end of the probe against the far end of the body cavity. Such a probe is therefore able to treat a greater portion of the interior tissue of a body cavity, without having to resort to multiple, specialized resection probes. Ideally, at least a portion of the electrically conductive surface is within the field of view of the imaging mechanism, thereby facilitating the optical directing of distal tissue ablation.

In a further aspect, the present invention provides a tissue resection device comprising a shaft having an aperture adjacent to a distal end, and a lumen extending from the aperture to a proximal end of the shaft. A cutting member is disposed adjacent to the aperture, and defines a plurality of lobes which simultaneously removing a plurality of tissue strips from a body cavity. Typically, the cutting member comprises an electrosurgical wire having a plurality of loops. Ideally, the outer perimeter of the cutting member is rounded to facilitate removal of a sheath disposed over the shaft proximally of the aperture.

The invention further provides a method for resecting tissue from a surgical site of an internal body cavity, the method comprising cutting strips of tissue from the surgical site by axially translating a cutting member of a probe. Fluid is aspirated from the surgical site and into a radially oriented aperture on a shaft of the probe so that the strips of tissue enter the aperture. The strips are chopped into tissue fragments as they enter the aperture, which tissue fragments are evacuated through the shaft of the probe. Generally, irrigation fluid flows over an imaging mechanism toward the cutting member while optically imaging the tissue and cutting member through the imaging mechanism, and also while cutting the strips of tissue toward the imaging mechanism. Preferably, the cutting member is translated proximally relative to the imaging mechanism, thereby allowing the strip of tissue to be cut while optically viewing the procedure from a fixed frame of reference.

In some embodiments of the method according to the present invention, tissue which is disposed distally of the distal end of the probe is ablated with a distally oriented electrically conductive surface. Generally, the electrically conductive surface is swept over proximally oriented tissues. Alternatively, the electrically conductive surface is rolled over proximally oriented tissue, the electrically conducted surface comprising a rolling element. The electrically conductive surface may conveniently be mounted to the cutting member by removing the cutting member through a sheath from the body cavity.

In a first aspect, the present invention provides a method for extracting tissue from the uterus, the method comprising removing tissue from the uterus by applying a radio frequency to the tissue so that a portion of the removed tissue is vaporized. While removing the tissue, the depth of tissue removed from the uterus is viewed and the removed tissue is evacuated from the uterus. Preferably, the radio frequency is applied by an electrosurgical member of a probe, the probe also having an imaging mechanism and an aspiration lumen. Ideally, these probe elements provide an irrigation flow path that maintains image quality during simultaneous removal and evacuation.

Generally, a member is translated through uterine tissue while the member is energized with the radio frequency to vaporize tissue adjacent the member. In some embodiments, the member severs unvaporized tissue from the uterus, the severed tissue ideally being either fragmented or morcellated within the uterus to avoid clogging of the aspiration lumen. In other embodiments, substantially the entire removed tissue is vaporized, preferably with a member comprising at least one rollable element. Particularly advantageous rollable elements direct energy into the uterine tissue to fragment and remove a large swath of tissue with each pass of the member, for example, rollable elements which have spurs, or a plurality of fanned out disks.

In another aspect, the present invention provides an electrosurgical device comprising a shaft having a proximal end, a distal end, an aperture near the distal end, and an aspiration lumen between the aperture and the proximal end. An electrosurgical member is disposed near the aperture, the member vaporizing tissue from an internal surgical site when the electrosurgical member is energized and translated through a target tissue. An imaging mechanism disposed on the shaft is oriented toward the electrosurgical member so as to view the target tissue without substantial interference from tissue debris when the electrosurgical member vaporizes tissue while the vaporized tissue is being aspirated through the aperture.

In a still further aspect, the present invention provides a tissue resection device comprising a shaft having a proximal end and a distal end, with an electrosurgical cutting member disposed near the distal end of the shaft to sever tissue as the shaft is translated. An electrically conductive surface, typically comprising a roller, is disposed near the cutting member to apply coagulative or ablative energy to a severed surface of remaining tissue. Preferably, the cutting member comprises a transverse cutting wire, the wire and the roller typically protruding radially from the shaft and axially aligned. This arrangement facilitates rolling of the conductive cauterizing surface across any open blood vessels directly after the tissue strip is removed, separating the cutting and cauterizing functions into two independently optimized structures and power systems, and also minimizing the drag encountered during each stroke of the probe. Ideally, the conductive surface is removably mounted to the shaft, thereby avoiding any interference to the cutting process when coagulation and/or ablation is not required.

In another aspect, the present invention provides a tissue resection device comprising a shaft having an aperture adjacent to a distal end and a fluid and tissue aspiration lumen extending from the aperture to a proximal end of the shaft. A cutting member is disposed adjacent to the aperture to sever tissue as the shaft is translated, and a chopping mechanism disposed within the lumen of the shaft reduces the size of tissues passing through the lumen. An electrically conductive surface is disposed near the cutting member to apply coagulative or ablative energy to a surface of remaining tissue. Preferably, the cutting member comprises a transverse electrosurgical cutting wire, at least a portion of the aperture ideally being disposed between the wire and the conductive surface. In a particularly advantageous embodiment, the conductive surface comprises a transverse roller aligned with the wire so that as the wire severs a strip of tissue proximally, the strip is directed into the aperture, after which the roller immediately cauterizes any open blood vessels.

Ideally, interference between the cutting member and the conductive surfaces is avoided by removing the conductive surface from the probe when it is not needed. Such a structure also promotes the use of specialized conductive surfaces which are removably mountable onto the probe, such as rollers, balls, distal ablation surfaces, and the like. Generally, the conductive surface extends resiliently beyond the wire so that the conductive surface may be used alone or deflected out of the way of the cutting member. Such a resilient mounting may also help maintain contact between the conductive surface and the remaining tissue surface during variations in cutting depth, and also at the beginning and end of each cut. In a final alternative, a retractable conductive surface will provide a flexible probe which need not be removed from the patient body to vary the cutting wire/conductive surface interaction.

BRIEF DESCRIPTION OF THE DRAWINGS

Other objects, features and advantages of this surgical instrument and accompanying procedure will become more apparent after referring to the following specification and attached drawings in which:

FIG. 2A is a section at the distal end of the probe illustrating the rigid shaft, elongate cutting aperture, infusion lumen, electrocautery cutting head, rotating cutting head driving tube with integral aspiration lumen, viewing optical fiber, and ultrasound transducer;

FIG. 7 is a detail of the probe at the point of attachment to the housing illustrating the disposition of the sieve for capture of the chips or morsels from surgery and illustrating how the disposable probe can be shipped (intact or bent) for compact shape for transport for biopsy of the retained chips or morsels;

FIG. 8 is a section along lines 8—8 of FIG. 7 illustrating both the perfusion path and the aspiration path together with the relative locations of the probe, rotating tube, and path for the viewing optical fiber;

FIG. 11 is a detailed side view of an alternative embodiment of the device of FIG. 10 with an angled electrocautery loop;

FIG. 11A is a front end view of the device of FIG. 11;

FIG. 12 is an alternative embodiment of the device of FIG. 11 employing a wire director for directing removed tissue into the chopping mechanism;

FIG. 12A is a front end view of the device of FIG. 12;

FIG. 13 illustrates an alternative embodiment of the device of FIG. 12 with the optical scope and the ultrasonic transducer being separated;

FIG. 13A is a front end view of the device of FIG. 13; and

FIGS. 20A through 23B illustrate alternative cutting members for use with the probe of FIG. 15.

FIGS. 30 and 31 illustrate the axial cutting motion of the cutting member and morcellator, and also show the transverse arched wire supporting and fanning-out the rolling elements of the vaporizing member at the distal end of the probe of FIG. 28;

FIGS. 32A and 32B illustrate a disk-shaped rolling element for use in the vaporizing member of the probe of FIG. 28;

FIGS. 33–33B illustrate alternative rolling elements having a spurred cross-section for use in the vaporizing member of the probe of FIG. 28;

DETAILED DESCRIPTION OF THE SPECIFIC EMBODIMENTS

Figure 1A:
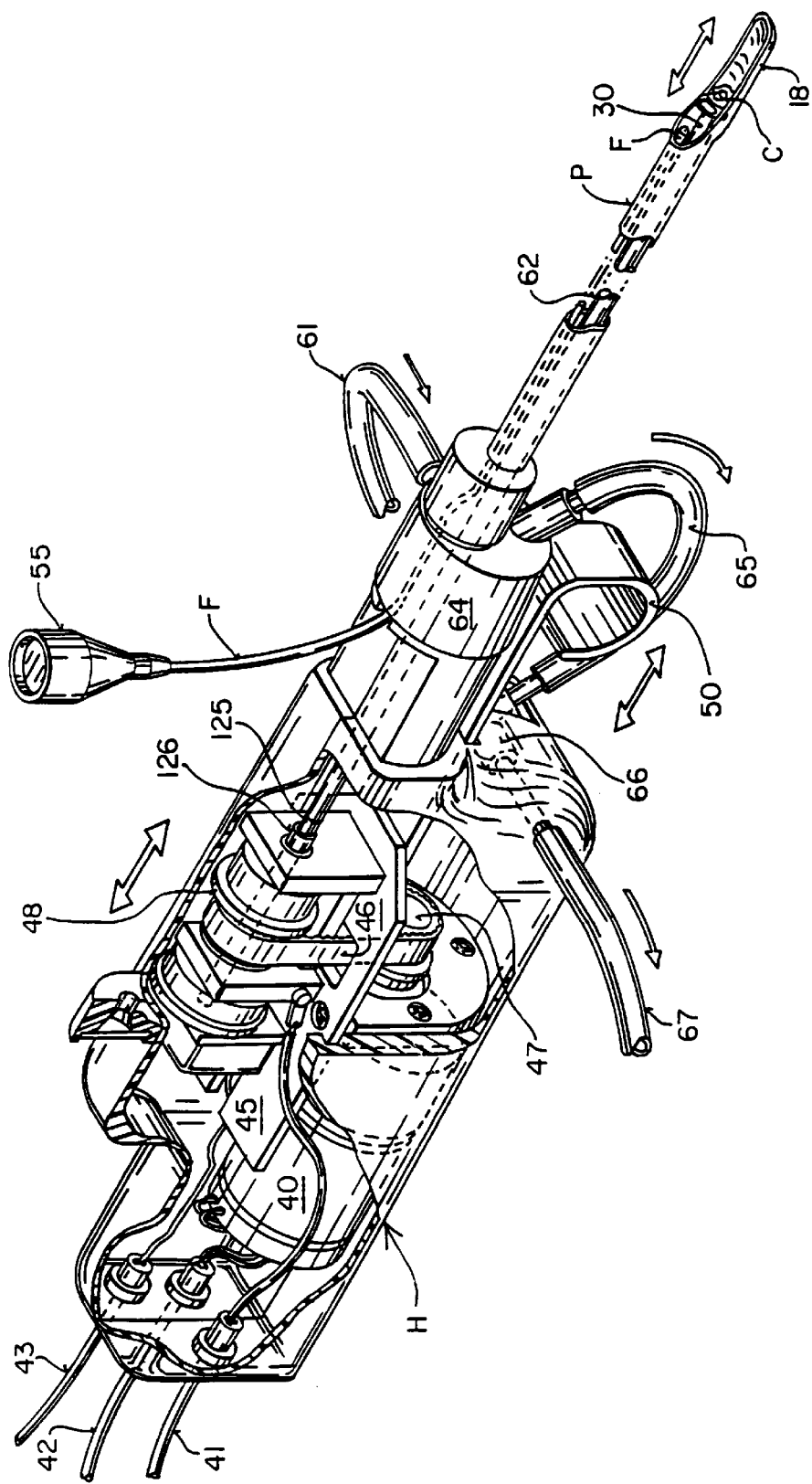
FIG. 1A is a perspective view of the drive housing with probe attached illustrating the housing and probe in partial section for understanding of the operative portions of the instrument.

Referring to FIG. 1A, surgical probe P is shown mounted to housing H. In understanding this invention, the probe P will first be discussed with respect to the preferred embodiment of FIG. 2A and 2B. Thereafter, the construction and operation of the probe from drive housing H in the hand of a surgeon will be discussed. Finally, alternate embodiments of the probe and cutting head as well as the capture of chips or morsels from the surgical site within the detachable probe will be set forth.

Figure 2B:
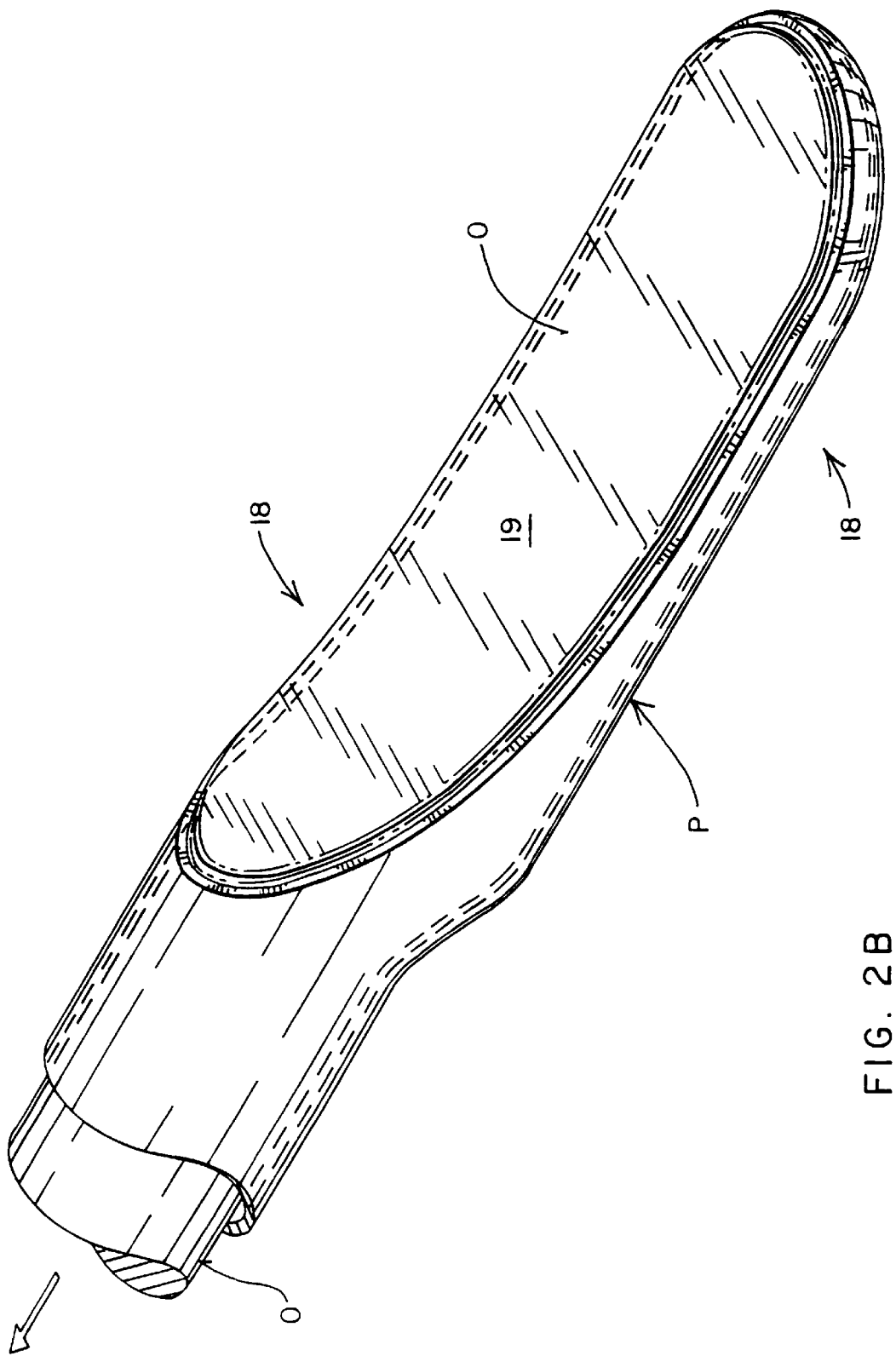
FIG. 2B is a perspective section similar to FIG. 2A with the cutting head removed, and an obturator in place for instrument insertion.

Referring to FIG. 2A and 2B, probe P is illustrated only at its distal and surgical end. Probe P is rigid having a blunted forward end 14 with an enlarged end 16 for fully accommodating the section of cutting head C. Exposure for surgery of cutting head C occurs at elongate slot 18 with view of the cutting head C during surgery within slot 18 being provided by optical fiber F at the proximal end of the slot. In FIG. 2B, probe P is disclosed occupied by obturator O. It is in this mode that probe P is inserted.

An electrocautery cutting head C is provided. Head C includes electrically conductive cutting edges 20 which are radially exposed from the cutting head C for surgical resection when head C is rotated in the direction of arrow 22. The electrical current is concentrated at the cutting surface, and heat generated from the resistance of tissue to the flow of electrical current is high enough to vaporize cells near the cutting surface. Head C is hollow and communicates to rotating driving tube 30 with interior aspiration lumen 25. An ultrasound transducer T rotates with cutting head C and sends and receives acoustical signals through wire 35. This transducer can measure remaining uterine wall thickness immediately after surgery when head C is in elongate slot 18 drawn proximally or distally of elongate slot 18 or at any intermediate position with respect to the slot.

Cautery alone utilizing probe P can occur. Specifically, by rotating cutting head C opposite to arrow 22, electrocautery cutting heads 20 pass in a blunted and non incisive path over the flesh. Cautery results.

Having generally discussed the construction of the probe, attention can now be directed to handle H.

Referring to FIG. 1A, handle H includes DC motor 40 electrical connections 42—it being recognized that reversal in motor polarity causes reversal in motor direction. Electrocautery connection is routed via a standard cautery power supply through conduit 41 to a journal bearing connection (see FIG. 1A). Acoustical transducer T (seen in FIG. 2A) at cutting head C sends and receives electrical signals through lead 43. A conventional slip coupling—not shown—is provided to wire 35 in tube 30 to lead 43.

Motor 40 is mounted to plate 45 and provides driving rotation at toothed pulley 47. Belt 46 drives toothed pulley 48 which in turn rotates drive tube 30 through quick disconnect coupling 125. This quick disconnect coupling is the point of removable attachment of the probe. (See FIG. 7)

Drive tube 30 is of constant length. Forefinger trigger 50 attaches directly to plate 45 which is mounted for sliding translation interior of handle H. By movement of trigger 50 relative to housing H, corresponding movement of cutting head C occurs along elongate slot 18. Video camera coupler 55 communicates to fiber F having illumination strands for viewing of the applicable surgery.

Referring to FIG. 1A, the fluid circuit for maintaining uterine cavity distention is only illustrated in pertinent part. It is presumed that standard technology will be used to maintain required pressure for uterine cavity distention through inlet conduit 61. Inlet conduit 61 communicates to probe P in the infusion lumen 62. By maintaining a constant pressure sufficient to establish uterine distention, required inflation is maintained in the organ—here the uterus—in which the operation occurs.

Referring to FIG. 7, fluid exits the site of the surgery through lumen 25 in rotating tube 30 and passes to chamber 130 where chips or morsels from surgery are captured. Thereafter, aspirated fluid passes through conduit 65 to finger actuated valve 66 and thence to state of the art fluid capture apparatus. As is customary in such procedures, chips or morsels are routed to pathology for investigation including biopsies where required. The instrument may be shipped intact or be bent (as at shaft 30) for convenience. Disposal can thereafter occur.

Figure 1B:
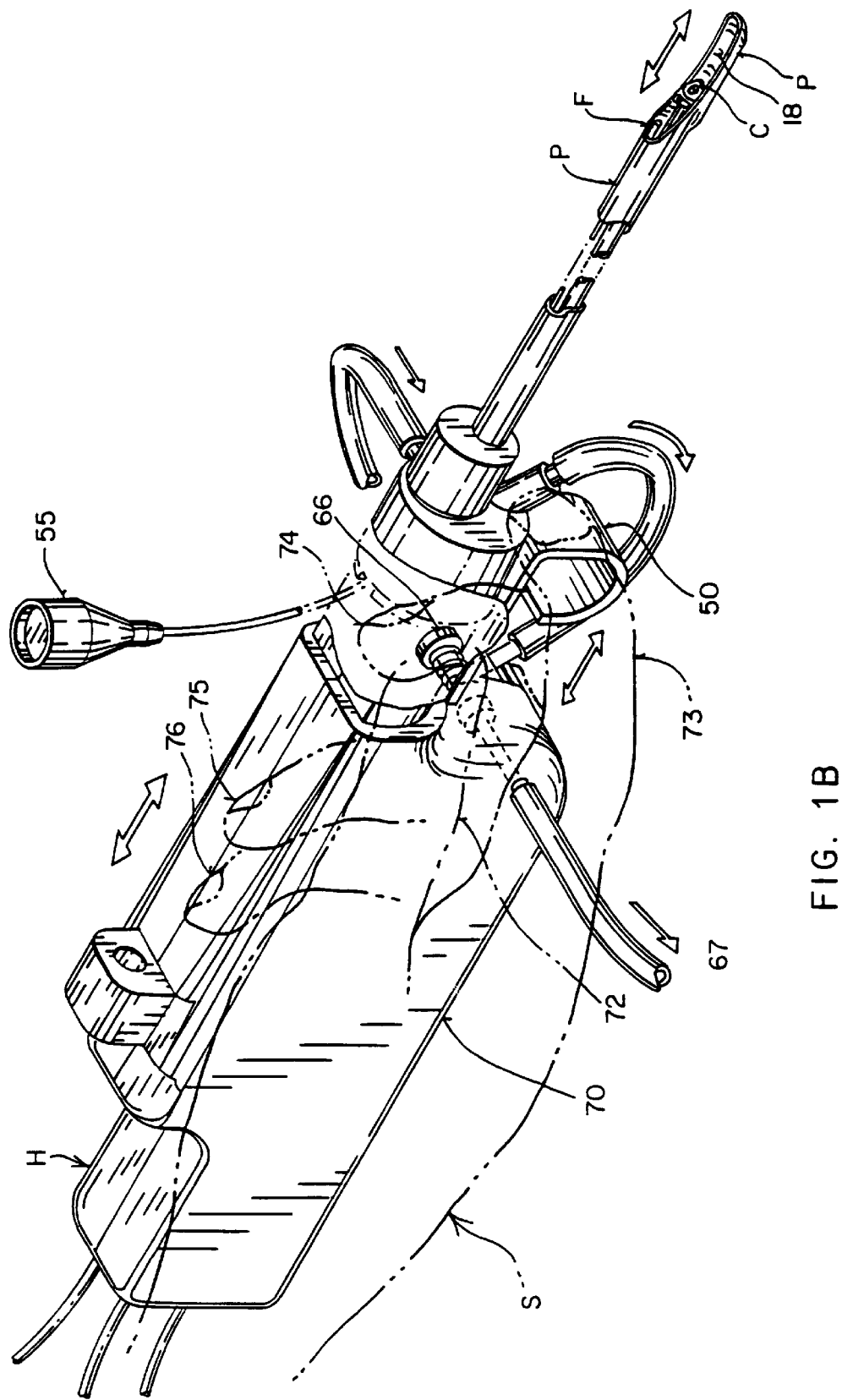
FIG. 1B is a perspective of the drive housing H with probe attached illustrating the housing grasped in the hand of the surgeon (shown in broken lines) demonstrating the surgical instrument manipulation of the rigid probe to dispose the elongate aperture at the surgical site, trigger finger manipulation of the cutting head relative to the viewing fiber and ultrasound transducer, and finger actuated aspiration during surgery.

Referring to FIG. 1B, the surgical ergonomics of housing H can be appreciated. Taking the case of a right handed surgeon, housing H at bottom surface 70 is held by hand S with thumb 72 opposing the third, forth and fifth fingers 74, 75 and 76. Forefinger 73 grips trigger 50 and by movement of finger 73 relative to housing H causes inward and outward traverse of cutting head C relative to elongate slot 18 of probe P. Middle finger 74 depresses valve 66 to cause applicable aspiration for example when view from eyepiece 55 indicates obstruction. Thus, flushing of sorbitol-mannitol solution distending the uterus can occur at intermittent and successive intervals as required by the surgical procedure.

Figure 3A:
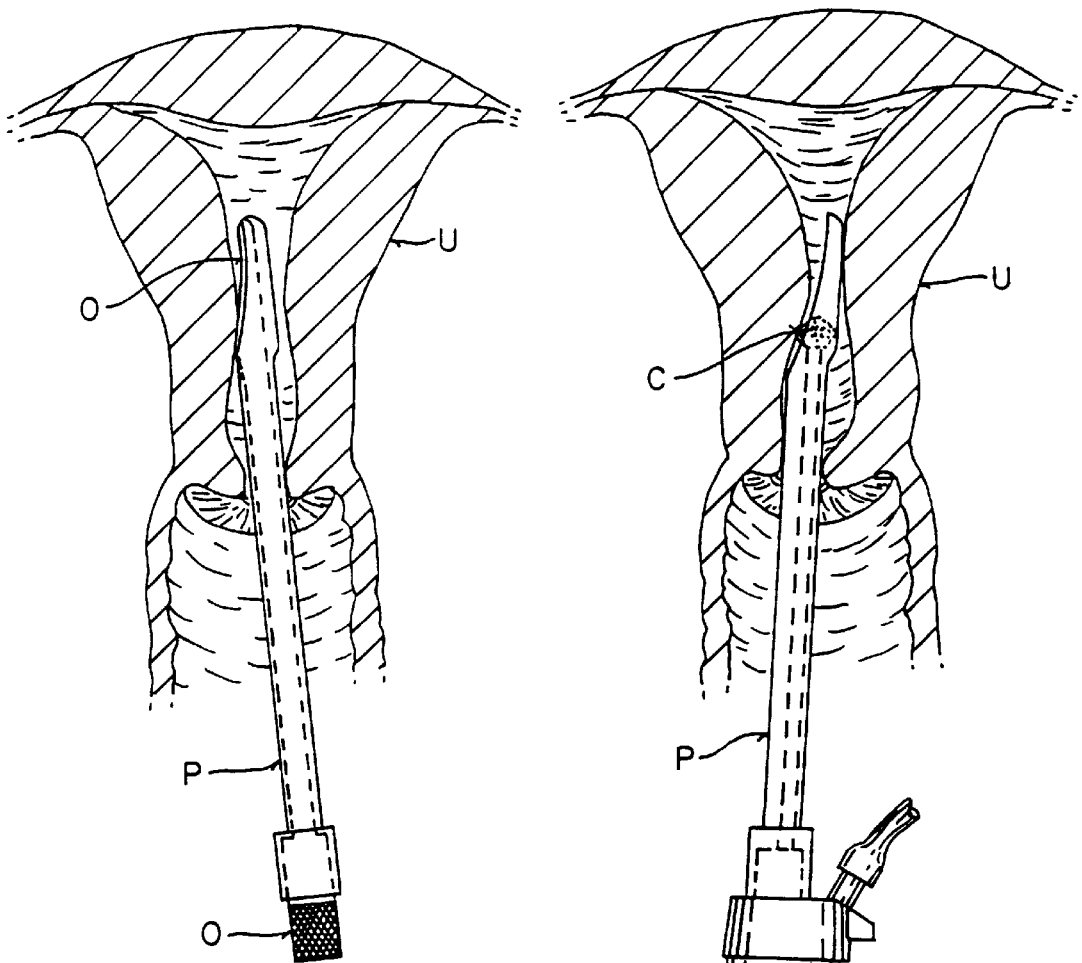
FIGS. 3A, 3B and 3C are respective sections of a uterus respectively illustrating the probe with an obturator during insertion for surgery, the instrument with rotating shaft and cutting head being inserted to the probe; and the insertion of the optical fiber for completion of the assembled probe.
Figure 3B:
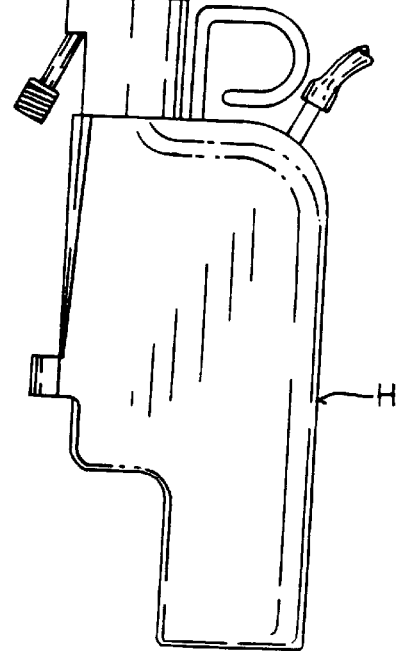
Figure 3C:
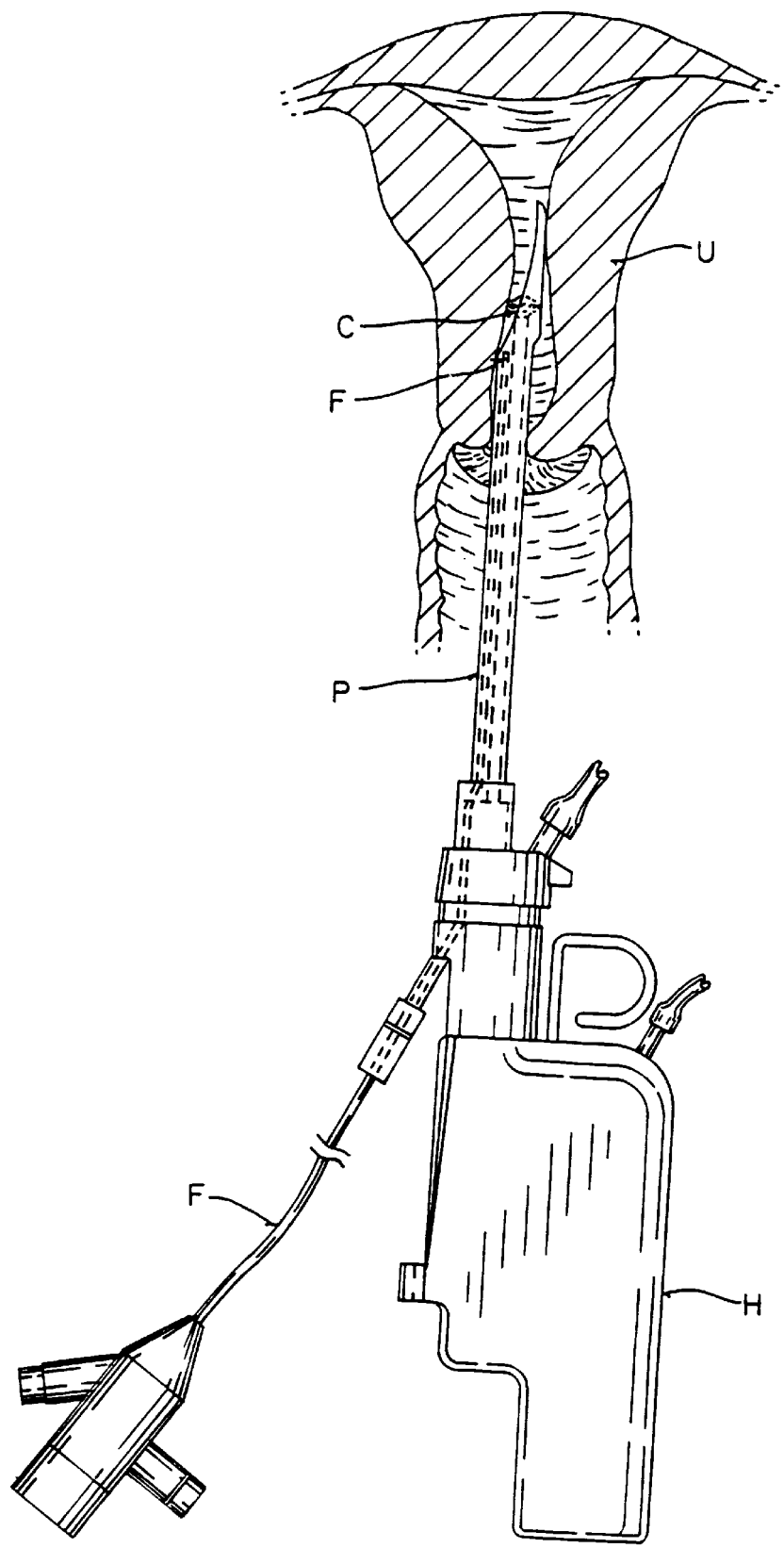
Figure 4:
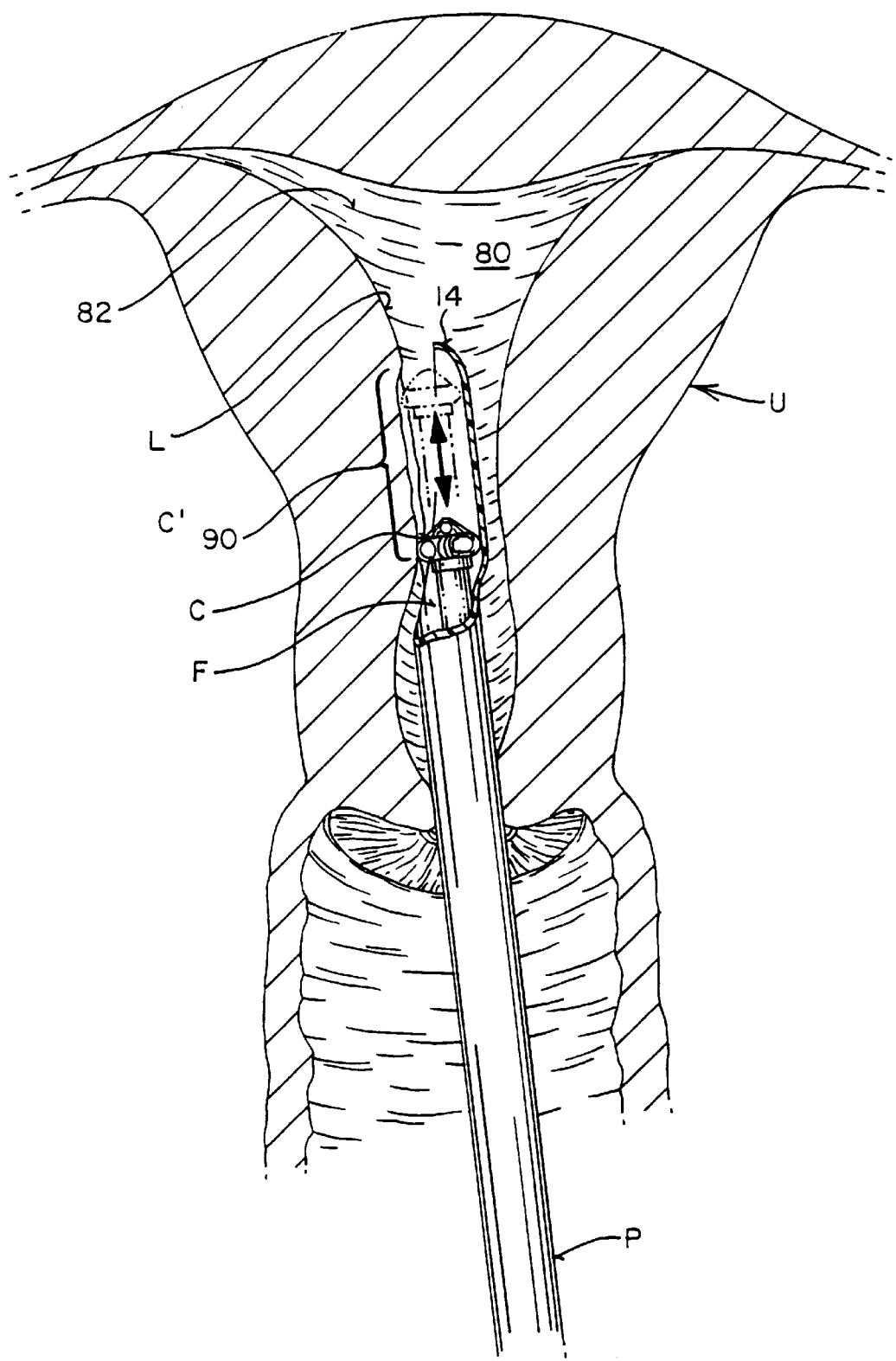
FIG. 4 is a section similar to the sections of FIGS. 3A–3C illustrating the working end of the instrument at an operative site.

Insert of the instrument is easy to understand. Referring to FIG. 3A, probe P with obturator O is inserted to uterus U. Thereafter, obturator O is withdrawn, and housing H with cutting head C threaded (See FIG. 3B). Once this insertion is made, fiber F is thereafter inserted for visualization of the surgical site (See FIG. 3C and the section of FIG. 8). Operative movement of the instrument can thereafter occur as illustrated in FIG. 4. The instrument in use can be visualized in the uterine section of FIG. 4. Probe P is shown with blunt end 14 within uterine cavity 80. This cavity is flooded with sorbitol-mannitol solution 82 so as to dispose lining L for surgery. In the preferred method, cutting head C is disposed at C'. Under the guidance of fiber F, probe P is maneuvered to surgical site. Assuming resection, cutter head C is drawn proximally of elongate slot 18 in probe P. With the preferred construction illustrated in FIG. 4, three occurrences follow.

First, and starting with cutting head C distally of elongate slot 18, view of the tissue before resection is provided. Secondly, and with traverse of cutting head C, surgical resection occurs. Thirdly, and immediately in the wake of the required resection, acoustical transducer T interrogates uterus U immediately after the surgery.

It will be remembered that evacuation of fluid occurs directly from the cutting edges of cutting head C to rotating tube 30 with its aspiration lumen 25. Accordingly, flushing of chips and morsels is immediate the surgical site 90 with minimal chance for clouding the required view through fiber F.

Figure 5:
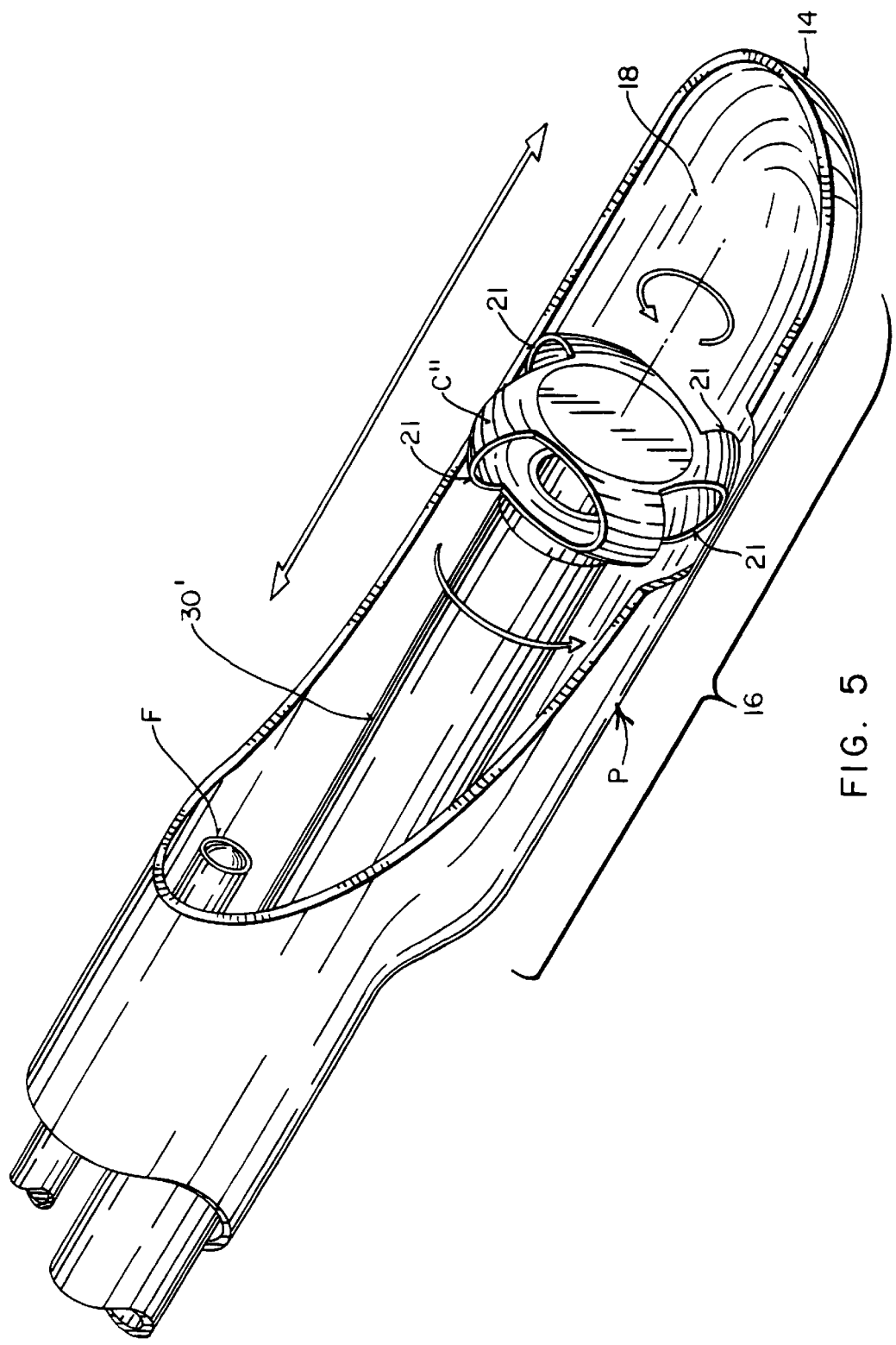
FIG. 5 is a section similar to FIG. 2A of an alternate embodiment of the probe here illustrated with a conventional cutting head without ultrasound interrogation.

Referring to FIG. 5, an alternate embodiment of cutting head C" is illustrated. Cutting head C" is hollow, attached to rotating tube 30', and included semi-spherical cutting edges 21. It will be noted that this head does not include acoustical transducer T nor does it include electrocautery. While both these features are preferred, they are not required.

It is to be understood that acoustical interrogation of uterus U immediately after surgery is not trivial. Specifically, and during the illustrated procedure utilizing operating tools and procedures of the prior art, one of the most difficult assignments of the surgeon is not to cut entirely through the uterus. Such cutting causes morbidity such as iatrogenic uterine perforation and can damage nearby body structures such as bowel.

Fortunately, soft tissue organs such as uterus U can be acoustically interrogated for their remaining wall thickness after resection. Thus transducer T can output through conventional acoustical visualizing apparatus the thickness remaining of the organ. Additionally, and with a conventional shaft encoder, an acoustical section or well known "B" scan of the section at the angle of view of the transducer can be displayed. For example, the remaining width when below a predetermined thickness can be utilized with its telltale acoustical signal to trigger an alarm warning the surgeon when remaining thickness is below a set tolerance.

Figure 6B:
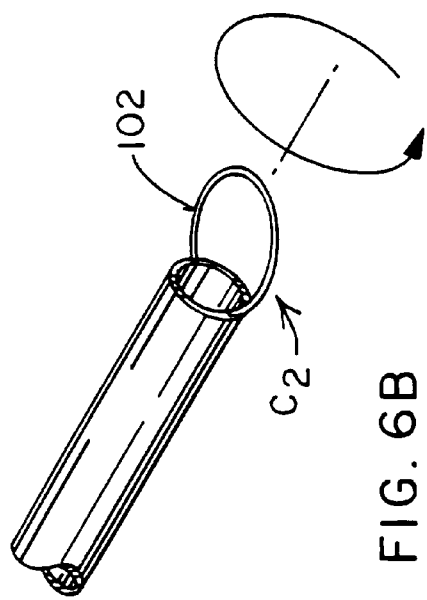
FIGS. 6A–6C are differing cutting heads utilized with this instrument.
Figure 6A:
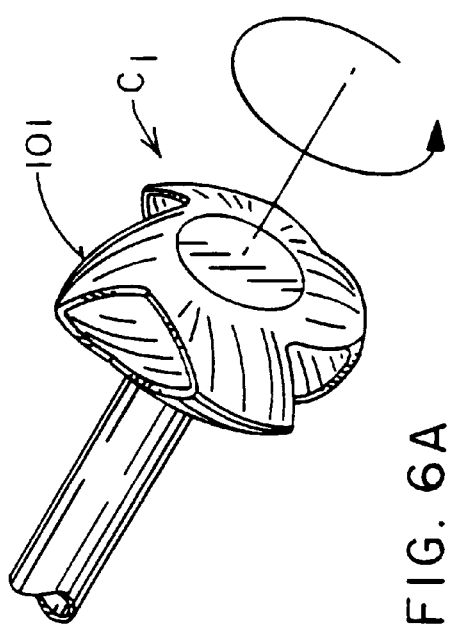
Figure 6C:
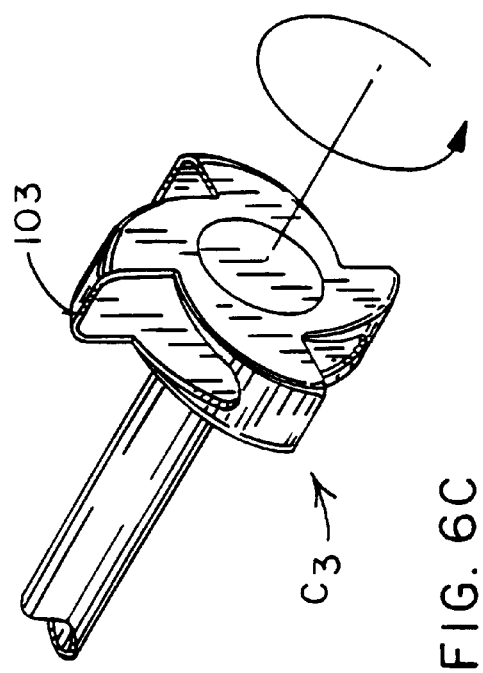

It will be apparent that the tool of this application will admit of a number of differing cutting heads. For example, as indicated in FIG. GA, it may be desired to have the cutting head end in a V-shaped cutting profile 101. Further and as set forth in FIG. 6B, and with modification to the probe, a rotating U-shape cutter 102 may be required for distal or end-on access to surgical sites. Finally, and as set forth in FIG. 6C, a flat cutter 103 is shown. It will be realized that this invention will admit of other shapes. Further, the respective cutting heads can either be conventional knives or be provided with suitable paths for electrocautery.

Referring to FIG. 7, the aspiration of fluid from the surgical site together with the trapping of morsels from surgery from the aspirated fluid can be understood. First, perfusion fluid is introduced through conduit 61 into perfusion chamber 100. It then enters probe P.

Viewing FIG. 8 at this juncture can be instructive. Specifically, bearing member 102 with fiber F and rotating tube 30 receiving concavities is placed interior of probe P and extends almost the full length of the lumen within probe P. It includes a lower round aperture 107 which is the surface against which rotating shaft 30 bears. The upper surface forms a saddle which locates and guides the viewing scope F which may be flexible. The remaining interior volume of probe P forms a channel which contains the perfusion fluid. Exit of the fluid occurs through slot 18 and the end of probe P.

Rotating shaft 30 extends completely through chamber 100 and into and through a housing defining chamber 130. Chambers 100 and 130 may be separated by an C-ring (See FIG. 7) or other suitable seal. It is in this housing that the morsels from surgery are trapped. Thereafter, shaft 30 terminates at a quick disconnect coupling 125 which couples to a counter part coupling member 126 driven by motor 40. (See FIG. 1B for this detail).

Interior of chamber 130, shaft 30 is provided with an aperture 128. Aperture 128 allows aspirated fluid to be communicated to chamber 130. Aspirated fluid is withdrawn from chamber 130 through conduit 65. Conduit 65 communicates through valve 66 and outflow conduit 67 for the discharge of aspirated fluid. (See FIG. 1B for valve 6 and conduit 67)

Screen 135 divides chamber 130 between aperture 128 (which rotates with shaft 30) and conduit 65. As a consequence, morsels from surgery are trapped on screen 135. This being the case, the attached probe P when removed from handle H can constitute both a disposable appliance as well as a convenient cartridge 64 for transport of surgical morsels for biopsy. (See FIG. 1A and 7)

As is apparent, the disposable portion of the device may or may not include probe P.

As a known alternative to the cautery illustrated herein, heated fluids can be flowed through the instrument to coagulate the tissue.

The preferred and illustrated application of this design is for trans-cervical fibroid removal, removal of myometrium, and removal of endometrium. Other uses of instruments substantially incorporating this design are listed below:

Intrauterine (Hysteroscopy)
    Uterine wall Resection
    Endometrial Ablation
    Endometrial Resection
    Submucous Myoma Resection
    Intramural Myoma Resection
    Transmural Myoma Resection
    Resection of Cervix and Cervical Canal
Kidney Resection (Laparoscopy)
    Retroperitoneal
Prostate Resection (Cystoscopy)
Intra-abdominal (Laparoscopy)
    Uterine Myomectomy
    Ovary Resection
Lung tissue and Tumors (Thoracoscopy)
    Measuring Device (Ultrasonic Transducer)
    Uterine Wall Thickness
    Endometrium Thickness
    Prostate Thickness
    Intra uterine measurements
    Urethra thickness The above procedures may require relatively minor modifications of the disclosed device.

Figure 9:
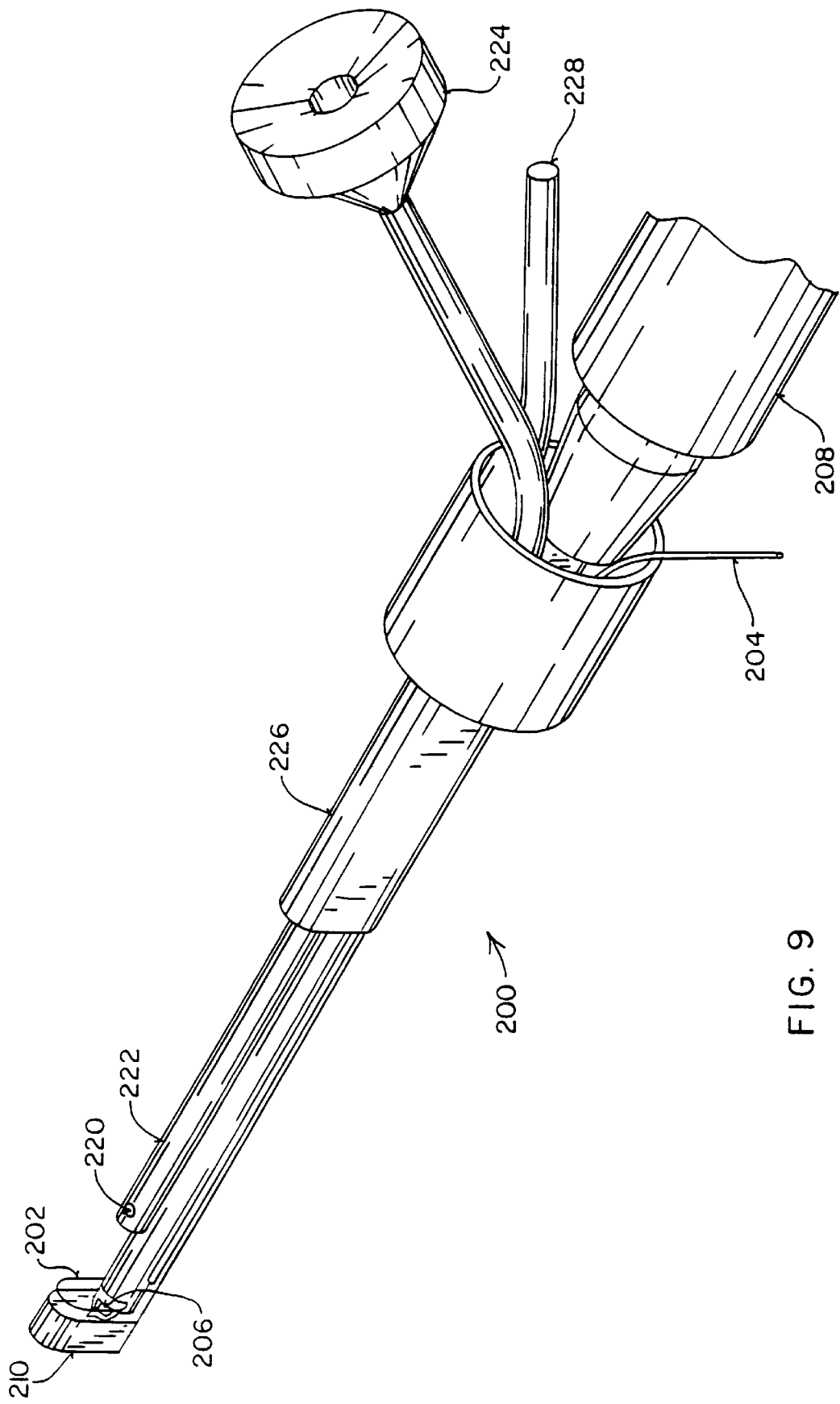
FIG. 9 is a schematic perspective view of an alternative tissue resection device according to the principles of the present invention.

The invention provides an alternative embodiment of a tissue resection/ablation device 200. The device 200 is illustrated schematically in FIG. 9. While the device 200 is particularly advantageous for trans-cervical fibroid removal, removal of myometrium, and removal of endometrium, the device 200 may find other uses including those previously listed above and further including joint arthroscopy. For purposes of convenience, the device 200 will be described with reference to treatment of the uterus. However, the invention is in no way limited to only this type of application.

The device 200 includes an electrosurgical member 202 that is shown schematically in the form of an arch. The electrosurgical member 202 can conveniently be formed from an electrically conductive wire, metal strip, or the like, and can be fashioned in any shape depending on the particular application. Fashioning in the form of an arch is advantageous when removing fibroid tissue from the uterus because strips of tissue can rapidly be removed by translating the electrosurgical member 202 through the tissue. Current is provided to the electrosurgical member 202 through a wire 204 which is in turn connected to an electrosurgical unit. The electrical current is concentrated at the cutting surface, and heat generated from the resistance of tissue to the flow of electrical current is high enough to vaporize cells near the cutting surface.

When electrosurgically removing tissue using prior art methods, the surgical site within the uterus rapidly fills with debris created from the removed tissue. Removal of this debris becomes imperative to allow the surgeon to maintain a clear view of the operation site. Prior art attempts to remove such debris include "sweeping" away the debris between cutting strokes, and periodically removing the electrosurgical device from the uterus to flush or suction away the debris. In the present invention, the removed tissue is immediately evacuated from the uterus by directing the tissue strips from the electrosurgical member 202 and into a chopping or severing mechanism 206. The chopping mechanism 206 in turn rapidly reduces the size of the tissue strips so that the tissue can be suctioned through the device 200 and removed from the uterus. In this way, tissue removed by the electrosurgical member 202 is evacuated from the surgical site as rapidly as the surgeon can cut the tissue. The amount of debris created in the uterus is drastically reduced, and the time consuming steps of "sweeping" away tissue or removing the electrosurgical device from the uterus for flushing or suction is eliminated.

The tough and gristly nature of fibroid tissue makes it difficult to remove from the uterus with conventional knife-edged instruments. Use of the electrosurgical member 202 has proven to be effective in such removal. However, once removed by the electrosurgical member 202, the fibroid tissue becomes easier to process, and a conventional arthroscopic cutter can be employed to chop or sever the tissue into smaller morsels. Suitable arthroscopic cutters are described in U.S. Pat. Nos. 4,274,414 and 4,203,444, the disclosures of which are herein incorporated by reference. Briefly, such cutters include a rotating concentric tube having a shaving port into which the tissue is directed. The rotating blade chops the fibroid tissue into small transportable morsels or chips which can then be removed from the uterus through the concentric tube by suction. Although such cutters are preferred, a variety of different chopping mechanisms can be employed including reciprocating blades, grinders, and the like, a necessary requirement being that the mechanisms chop, severe or reduce the tissue into smaller morsels for evacuation. A motor 208 is provided to rotate the chopping mechanism 206. The motor 208 further includes a vacuum valve and an associated vacuum port for providing suction to remove the chopped tissue from the uterus.

To assist in directing the strips of tissue removed by the electrosurgical member 202 towards the chopping mechanism 206, an end cap 210 is provided just distal to the electrosurgical wire 202. In this way, tissue removed when translating the electrosurgical member 202 is directed by the end cap 210 into the chopping mechanism 206. The chopping mechanism 206 in turn chops the tissue as it is fed from the end cap 210 so that substantially all tissue removed by the electrosurgical member 202 is chopped and removed from the uterus. Operation of suction and motor 208 without electrocautery allows the device 200 to extract loose floating debris that may have escaped the initial cutting/extraction process.

Visualization of the surgical site while removing tissue can be provided by an ultrasonic transducer 220 disposed near the electrosurgical member 202. The ultrasonic transducer 220 provides information on the thickness of the uterine wall where the fibroid material is being removed. By monitoring uterine wall thickness in this way, removal of fibroid material can be halted before perforating and damaging adjacent structures such as the bowel or bladder. The ultrasonic transducer determines wall thickness as previously described with transducer T. Briefly, a pulse signal is sent through the uterine wall and the time required to receive a return pulse is measured. Based on this measurement, the thickness of the uterine wall can be calculated. This information can be viewed on a conventional oscilloscope screen, or the thickness can be displayed numerically. To map the area of the uterine wall near the area where the desired cut is to be made, a plurality of such measurements are made. Based on this information, the surgeon can estimate the appropriate depth for the entire length of the cut. Instead of displaying the result of each individual measurement on a oscilloscope screen or displaying a numeric value, a "B" scan can be made and entered into a processor to produce a visual image of the uterine wall. The visual image can then be evaluated to determine the appropriate depth for the cut.

The ultrasonic transducer 220 can be used independently of the electrosurgical member 202, e.g., by removing the electrosurgical member 202 or by not actuating it, as a diagnostic tool. When used as a diagnostic device, the transducer 220 is used to map the a body organ from within the organ. For example, the transducer can be positioned within the endometrial cavity of the uterus and actuated to map the endometrial cavity and the uterine wall. In this way, abnormalities in the uterus can be diagnosed.

Visualization of the surgical site during operation of the electrosurgical member 202 can also be provided by a fiber optic scope 222 near the electrosurgical member 202. The fiber optic scope 222 provides conventional visual feedback through an eyepiece 224 to which a video camera is commonly coupled for display on a video monitor and for creating a tape record of the procedure. The fiber optic scope 222 and the ultrasonic transducer 220 can be used separately or can be used together to provide both conventional optical visualization and ultrasonic visualization of uterine wall thickness.

Standard optical scopes may also be used in place of the fiber optical scope 222. The tissue resection device 200 will usually be introduced into the cervix through a sheath 226. To facilitate introduction of the sheath 226, an obturator is usually first inserted into the sheath 226. Once the sheath 226 is inserted into the uterus, the obturator is removed from the sheath 226 and the device 200 is inserted into the sheath 226. The sheath 226 provides a working channel through which the electrosurgical member 202, the chopping mechanism 206, the fiber optic scope 222, the ultrasonic transducer 220, and other components of the device 200 can be inserted. When the components of the device 200 are introduced into the sheath 226, a seal is formed between the components of the device 200 and the sheath 226 (see FIG. 10). In this way, irrigation fluid can be applied through an irrigation tube 228 to distend the uterus before tissue removal, and to make up for fluid used in the extraction process.

Figure 10:
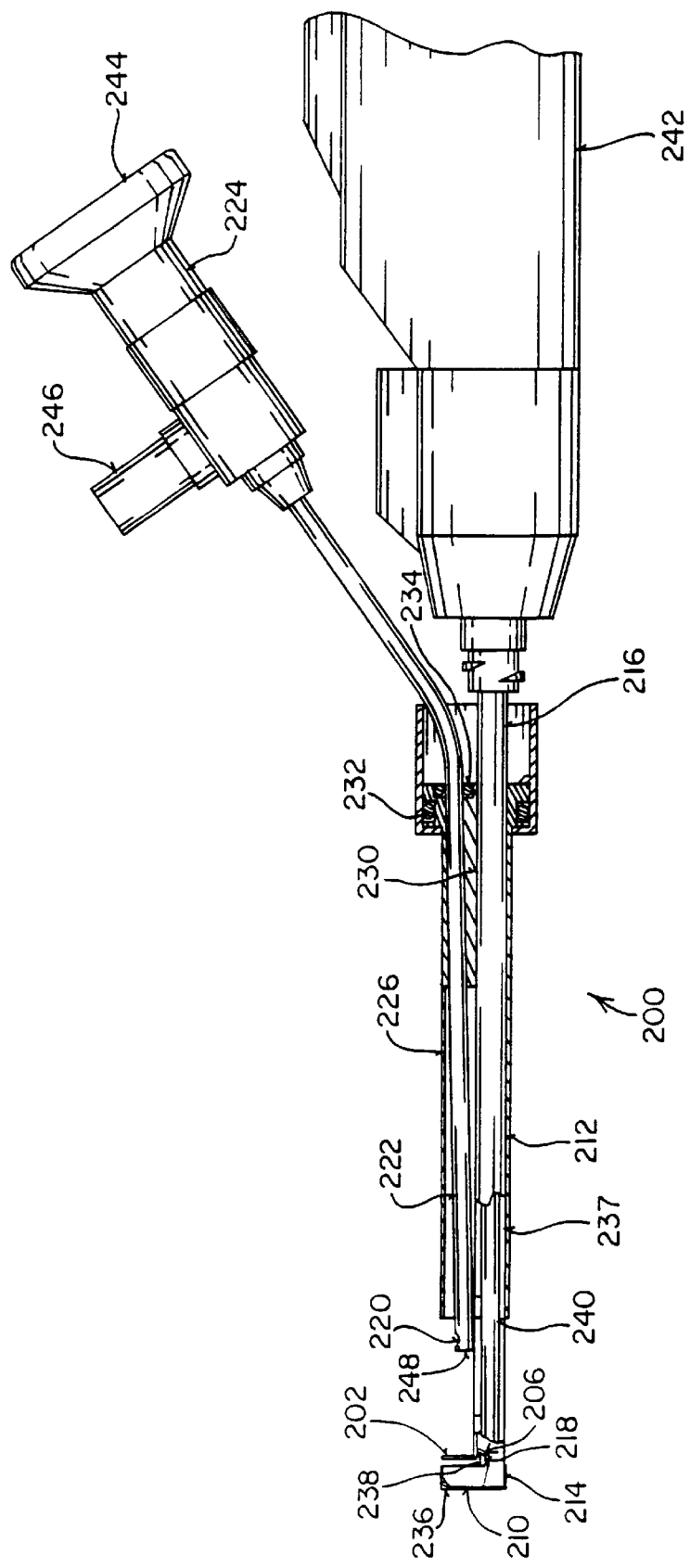
FIG. 10 is a detailed cut-away side view of an exemplary tissue resection device patterned according to the schematic of FIG. 9.

Referring to FIG. 10, an exemplary embodiment of a tissue resection device will be described. The device of FIG. 10 is patterned after the schematic of FIG. 9. For purposes of convenience, the embodiment shown in FIG. 10 will use the same reference numerals as used to schematically describe the tissue resection device 200 in FIG. 9. The device 200 includes an elongate body 212 having a distal end 214 and a proximal end 216. The elongate body 212 houses the chopping mechanism 206 and holds the electrosurgical member 202 in a fixed position relative to the chopping mechanism 206. To position the elongate body 212 and the fiber optic scope 222 within the sheath 226 (shown cut away to illustrate positioning of the components), a guide 230 is provided within the sheath 226. (For purposes of clarity, the irrigation lumen 228 and wire 204, which pass through channels in the guide 230, have been omitted.) The guide 230 is slidable within the sheath 226 and also provides a seal between the components and the sheath 226 so that distention pressure can be maintained inside of the uterus during operation. The guide 230 is preferably constructed of plastic, but can alternatively be constructed of a variety of other materials including stainless steel, brass, aluminum, and the like. The guide 230 is preferably permanently fixed to the outside of the elongate member 212 and includes O-rings 232 and 234 for sealing the guide 230 to the sheath 226 and scope 222. The sheath 226 will be preferably constructed of stainless steel which can be sterilized and reused.

The electrosurgical member 202 will preferably comprise an electrosurgical wire that is formed into a loop, an arch, or other suitable geometry. The electrosurgical wire 202 is attached to the outside of the elongate body 212 and is positioned above an aperture 218 in the elongate body 212 which provides access to the chopping mechanism 206. The end cap 210 is fixed to the distal end 214 of the elongate body 212 so that strips of tissue removed by the electrosurgical wire 202 are directed by the end cap 210 into the aperture 218.

An electrically conductive area 236 (or plurality of areas) is provided on the outside surface of the end cap 210 that can be connected to the same electrosurgical unit used to provide current to the electrosurgical wire 202. When actuated, the electrically conductive area 236 can be applied to bleeding tissue to promote coagulation to stop bleeding or can be used for endometrial ablation. When used for ablation, the end cap 210 will preferably be constructed of a ceramic, and the electrically conductive area 236 will preferably be a metallic surface on the cap 210 that is connected by a separate wire to the electrosurgical unit.

Figure 10A:
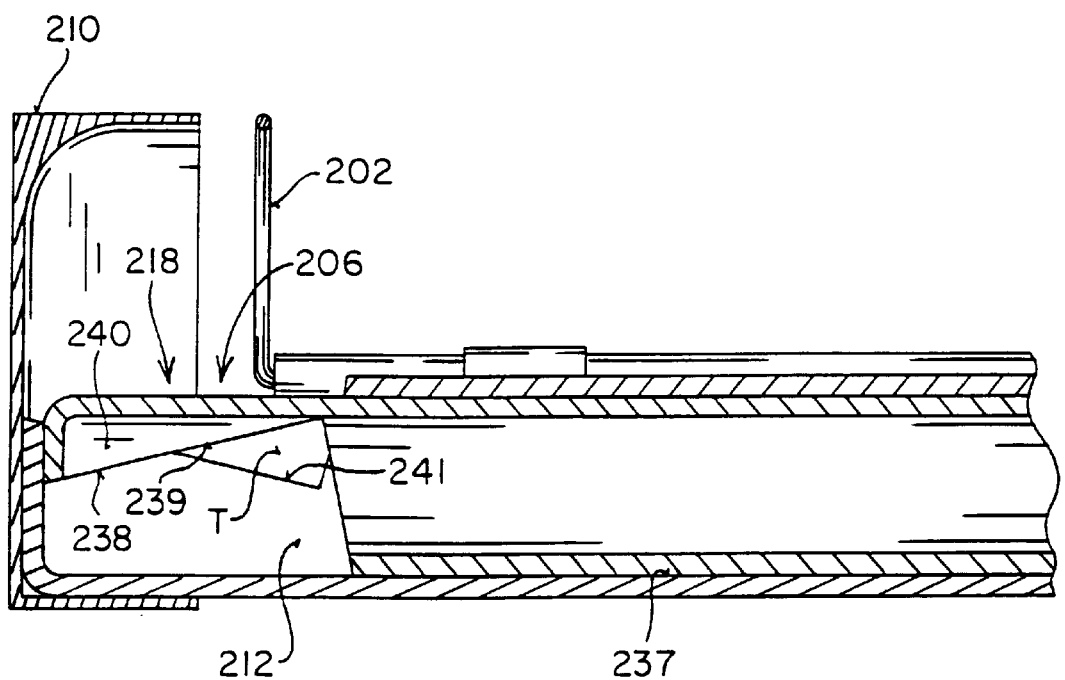
FIG. 10A is an enlarged cross-sectional view of the distal end of the tissue resection device of FIG. 10.

The elongate body 212 includes a central lumen 237 extending between the distal end 214 and proximal end 216. Held within the lumen 237 is the chopping mechanism 206. As shown best in FIG. 10A, the chopping mechanism 206 will preferably include a concentric rotating tube 240 disposed within the lumen 237. A shaving port 238 is formed in the wall of the tube 240 and is generally aligned with the aperture 218 of the elongate body 212. An edge 239 of the shaving port 238 and an edge 241 of the aperture 218 are sharpened so that any tissue drawn through the aperture 218 and shaving port 238 are sheared upon rotation of the concentric tube 240. In FIG. 10A, the rotating tube 240 is shown with the shaving port 238 facing away from the aperture 218. The triangle area TR is an opening between the edges 239 and 241. As the tube 240 is rotated, the edge 239 of the shaving port 238 is translated across the edge 241 of the aperture 218 until the triangle area TR disappears. Any tissue extending through both the shaving port 238 and the aperture 218 is sheared by the edges 239 and 241. Upon each revolution of the tube 240, another morsel of tissue is sheared.

The concentric tube 240 is rotated by the motor 208 (not shown) held within a housing 242. The housing 242 includes vacuum ports for connection to a house vacuum and associated vacuum valves for regulating suction. The suction is applied through the tube 240 thereby allowing the chopped morsels to be evacuating from the uterus.

In an alternative embodiment, the electrosurgical wire 202 can be slidably mounted on the elongate body 212, and a trigger mechanism can be used to axially translate the wire 202 in a smooth and controlled manner along the body 212. In this way, the wire 202 is translated relative to the scope 222.

The eyepiece 224 includes a viewing element 244 and an illumination connector 246. When the illumination connector 246 is attached to a suitable light source, light is provided to the optical fiber within the scope 222. This allows a surgeon to look through the viewing element 244 and visualize the operation site near the electrosurgical member 202. The ultrasonic transducer 220 is disposed on top of the optical scope 222 and is positioned so that its field of view includes the operative area above the electrosurgical wire 202. In this manner, the operative area where tissue is being removed by the electrosurgical wire 202 can be optically viewed by the scope 222 and the wall thickness can ultrasonically be visualized by the transducer 220. The optical scope 222 is slidably held within the guide 230 so that scope 222 can be axially translated to adjust the viewing area of both the scope 222 and the ultrasonic transducer 220. In an alternative embodiment, the ultrasonic transducer 220 can be provided on a separate instrument that is inserted parallel to the scope.

An important feature of the resection device 200 is that a variety of electrosurgical wire/end cap/chopper configurations can be employed to provide greater flexibility and effectiveness in treatments. One such alternative embodiment is the tissue resection device 200' shown in FIGS. 11 and 11A. The tissue resection device 200' is essentially identical to the tissue resection device 200 except for the end cap and the positioning of the electrosurgical wire. In the resection device 200' an electrosurgical wire loop 202' is angled toward the distal end 214 of the elongate body 212, preferably at any angle relative to the elongate body 212. Alternatively, the loop 202' can be angled away from the distal end 214 at any angle. Angling of the wire 202' toward the distal end 214 is advantageous when treating difficult to reach areas such as the top of the uterus. An end cap 210' is correspondingly angled so that the end cap 210' does not interfere with the cutting performance of the wire 202'. As with the previous embodiment, the end cap 210' serves as a director for directing tissue into the chopping mechanism 206.

Referring to FIGS. 12 and 12A, a further embodiment 200" of the tissue resection device 200 will be described, with a corresponding additional method for resecting. The resection device 200" is essentially identical to the tissue resection device 200' described in FIG. 11 except for the configuration of the end cap 210'. In the tissue resection device 200", an end wire 250 is provided at the distal end 214 of the elongate body 212. Use of the end wire 250 is advantageous in that it allows an optical viewing path for the optical scope 222 beyond the distal end 214 of the device 200". This allows for viewing of the area where the device 200" is being positioned in preparation for a cut. FIG. 12A represents a view from the distal end 248 of device 200". Although the view is partially blocked by the end wire 250 and the electrosurgical wire 202, sufficient space is provided between the wires so that a surgeon can view beyond the distal end 214 when looking through the eyepiece 224. A shell 252 is welded or bonded to the elongate body 212. Along with the end wire 250, the shell 252 serves to direct removed tissue into the chopping mechanism 206. The shell 252 can optionally be provided with electrically conductive areas which can be used to cauterize or thermally ablate tissue as previously described.

As shown in FIG. 12, the ultrasonic transducer 220 is included on the optical scope 222. Alternatively, as shown in FIGS. 13 and 13A, ultrasonic transducer 220 can be held in a shaft 260 separate from the optical scope 222. In such a configuration, the optical scope 222 will preferably be a 2 mm optical scope that is aligned with an aperture 256 in the end wire 250 so that optical visualization can occur beyond the distal end 214. Both the shaft 260 and the scope 222 are slidable within the sheath to allow the optical scope 222 and the ultrasonic transducer 220 to be adjusted independently of one another.

Figure 14:
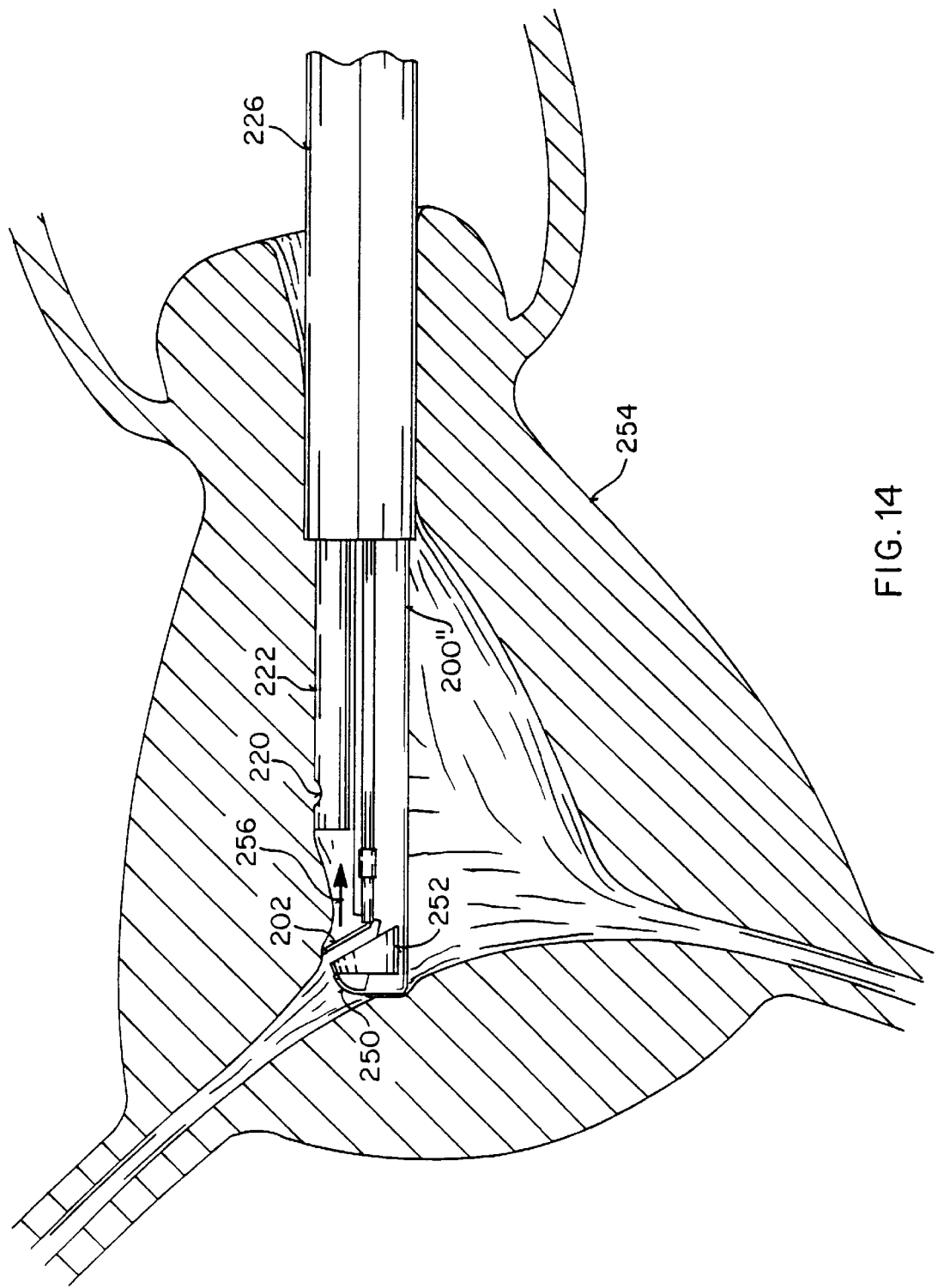
FIG. 14 illustrates an exemplary method for resecting tissue from the uterus using the device of FIG. 12.

Referring to FIG. 14, an exemplary method for using the tissue resection device 200" will be described. Although described in the context of the device 200" for convenience, the method can also be used with the previously described embodiments of the tissue resection device 200 and 200'. Initially, the sheath 226 is inserted into the uterus using an obturator (not shown) as previously described. The obturator is then removed and the device 200" is inserted into the sheath 226. Once a seal is formed between the sheath 226 and the guide 230, fluid is introduced into the uterus 254 for distention. While optically and/or ultrasonically viewing the uterus 254 with the fiber optic scope 222 and/or the ultrasonic transducer 220, current is delivered to the electrosurgical wire 202 and the wire 202 is translated along the lining of the uterus 254 as indicated by arrow 256. Alternatively, before commencing a cut, the ultrasonic transducer 220 can be actuated to survey and map the thickness of the uterus in the desired treatment area.

The wire 202 is translated by sliding the device 200" within the sheath 226. As the wire 202 is translated, strips of tissue are removed and directed to the chopping mechanism 206 by the end wire 250 and shell 252. The removed strips of tissue are then chopped into smaller morsels by the chopping mechanism 206 as previously described. After the completion of the first cut, the surgeon directs the electrosurgical wire 202 to an adjacent area and draws the wire through the fibroid. With the completion of each cut, the wire 202 is repositioned and another cut is begun. The amount of material removed is controlled by the manually maneuvering, e.g., lifting or pivoting, the device 200" to adjust the depth of penetration of the wire 202 into the uterus and by the length of the cutting stroke.

In this way, strips of removed tissue are automatically directed into the chopping mechanism 206 for removal from the uterus. This reduces the time and effort normally incurred in removing shavings which block the field of view of the surgeon. Further, since the device does not need to be withdrawn from the uterus 254 to remove the shavings, the task of reorienting the device 200" is eliminated. Fatigue is also reduced which allows the surgeon to perform more precise work.

The electrosurgical cutting wire described above is particularly well-suited for removal of strips of tissue from the uterus, prostate, or other internal body cavities. The rotating chopping mechanism then severs the strips of removed tissue into morsels, allowing the electrosurgical cutting wire and rotating chopping mechanisms to be independently optimized for these two distinct cutting operations. Generally, the strips are directed toward the chopping mechanism by a combination of an endcap and aspiration fluid flow into the chopping mechanism. Preferably, the endcap comprises a wire frame which improves optical visualization beyond the distal end of the probe, but any endcap structure protruding radially from the probe adjacent to the aperture has been found to decrease the cutting depth and increase cutting drag, particularly at the beginning of each cut.

Although the resection methods and devices described above have proven to be highly effective, electrosurgical resection methods could benefit from still further improvements. In a first aspect, although the frame endcap of the parent application provides a substantial improvement in distal optical visualization, some portion of the distal field of view remains blocked by this structure. In a second aspect, the electrosurgical cutting wire and chopping mechanism are most effective on tissues having a surface which is parallel to the probe axis, and it would be beneficial to incorporate some mechanism for treating tissues with surfaces disposed perpendicularly to that axis to facilitate treatment of the entire cavity without resorting to multiple specialized probes, articulation joints, or the like. In a third aspect, it has been discovered that the electrosurgical cutting wire may at times cut larger strips of tissue than are easily accommodated by the chopping mechanism for a given probe diameter. It would therefore be beneficial to increase the throughput of the chopping mechanism without having to decrease the quantity of tissue removed with each pass of the resector probe. Finally, it would be best if such improvements could be provided in a probe having the minimum possible weight and system complexity, utilizing existing operating room power systems to minimize costs, facilitate manipulation of the probe by the attending surgeon, and increase the reliability of the resection apparatus.

Figure 15:
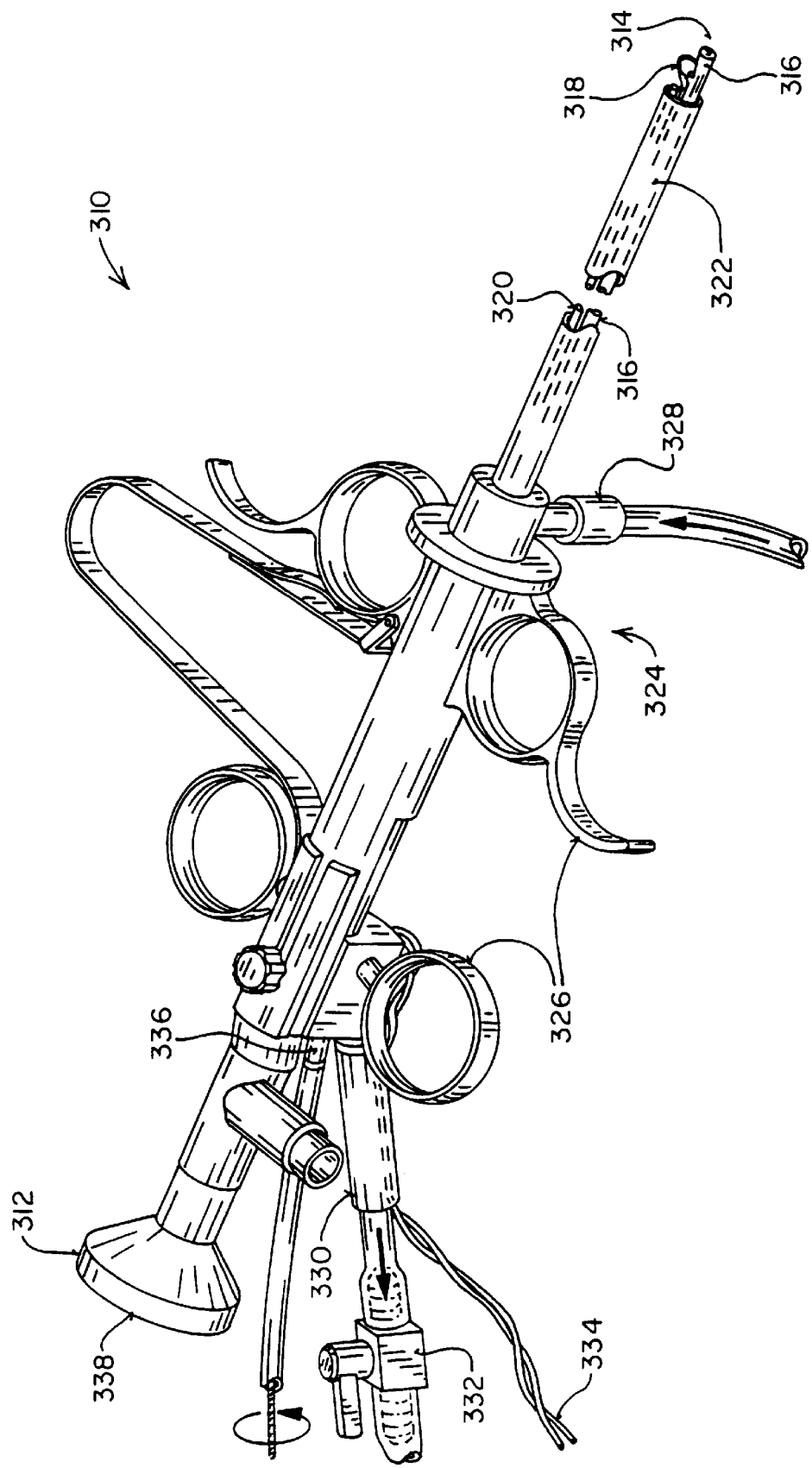
FIG. 15 is a perspective view of a resection probe according to the principles of the present invention, showing the proximal handle and several of the probe system connections.

Referring now to FIG. 15, resection probe 310 generally has a proximal end 312 and a distal end 314. A probe shaft 316 supports a cutting member 318 near its distal end. A fiber-optic or conventional imaging scope 320 is distally oriented toward cutting member 318, and runs proximally within sheath 322.

A probe handle housing 324 includes an actuation handle 326 for axially translating the shaft and cutting member relative to the sheath. An irrigation fluid port 328 and aspiration port 330 provide a continuous flow path for a clear, non-conductive fluid such as sorbitol-mannitol, mannitol, glycine, or the like. Aspiration flow is controlled by an aspiration valve 332, so that the distension pressure may be maintained independently from flow. Electrosurgical connector wires 334 and a flex drive input 336 provide external electrical and mechanical power, minimizing the weight of housing 324. An optical image eyepiece 338 is removably attached to housing 324 to optically direct the resection procedure. Optionally, an ultrasound transceiver may be mounted on the distal end of the probe as is more fully explained above. Such a distal ultrasound transducer may optionally comprise a one- or two-dimensional phased array to allow scanning of the resection tissue independent of any mechanical movement of the transducer probe.

Figure 16:
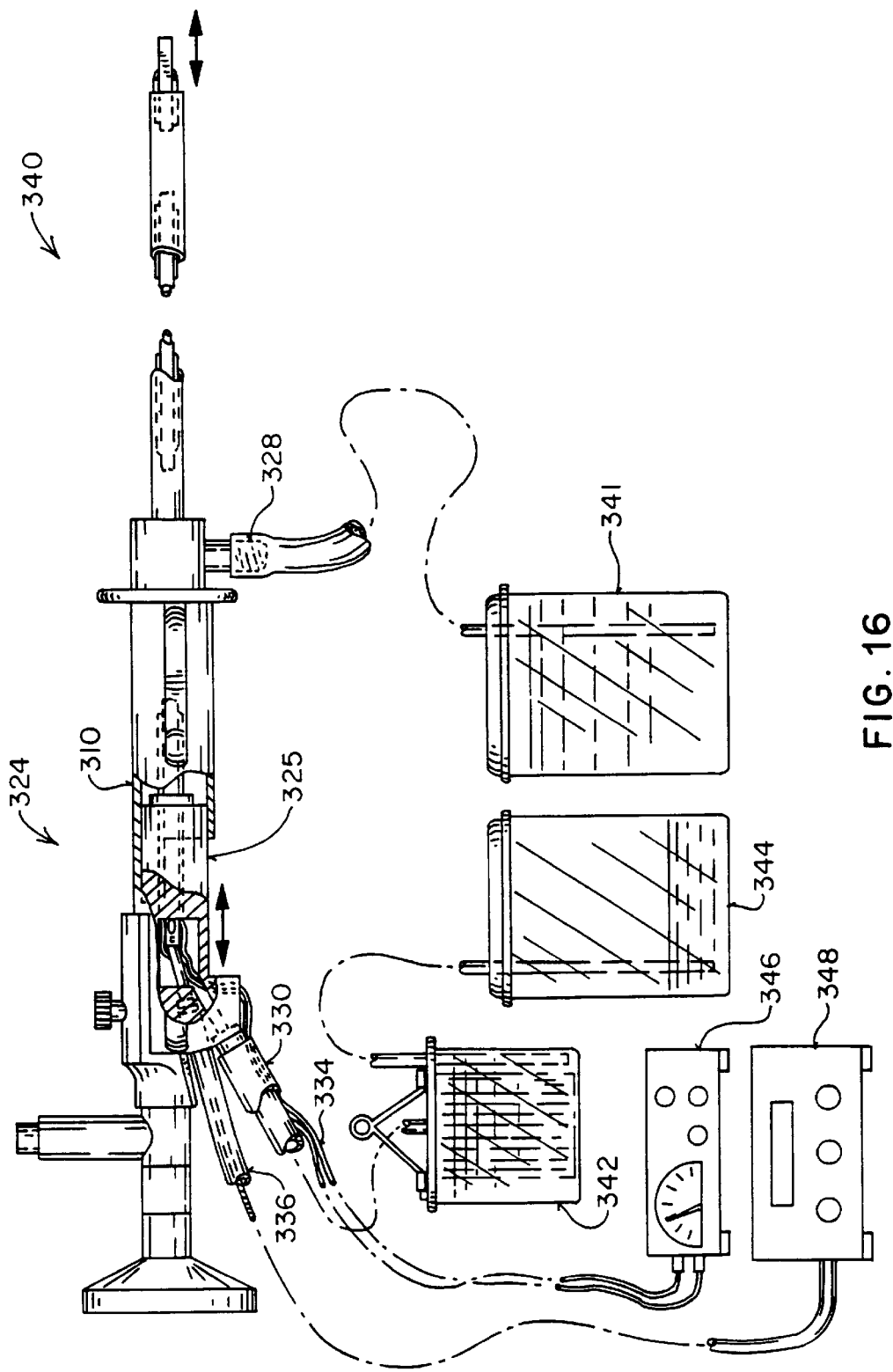
FIG. 16 illustrates a resection probe system, including the probe of FIG. 15.

Referring now to FIG. 16, a resection system 340 utilizes the input and output connectors on the housing of probe 310, together with standard stand-alone surgical system components to minimize cost, weight, and fatigue when using probe 310 in a resection procedure. An irrigation supply 341 is connected to irrigation port 328 to provide a continuous flow of irrigation fluid during resection. Preferably, irrigation supply 341 comprises a standard irrigation supply bag suspended above the surgical site to provide a constant pressure gravity feed, allowing distension pressure to be varied simply by changing the height of the irrigation supply. Alternatively, a valve or controlled flow pump may be used to supply irrigation fluid.

In the exemplary embodiment, aspiration, mechanical rotation, and electrosurgical potential are coupled to the shaft through a disposable cartridge 325 on shaft housing 324, the disposable cartridge reciprocating with the shaft as shown. Fluid which leaves aspiration port 330 is directed through a filter canister 342 and then to an aspiration sump 344. Filter 342 removes the solid tissue fragments from the aspiration fluid for analysis. Sump 344 is preferably connected to a standard vacuum supply line to promote the withdrawal of aspiration fluid through the probe. Aspiration vacuum control is conveniently provided by aspiration valve 332 (see FIG. 15).

Mechanical power is supplied to flex drive input 336 by drive motor 348. Drive motor 348 preferably rotates at least in the range between 500 and 1500 rpm, and typically allows for rotation in either direction, or oscillating rotation back and forth. The chopping mechanism generally shears tissue mechanically, without requiring electrosurgical potential.

Controlled electrosurgical power is supplied through electrosurgical wires 334 to the cutting member by power unit 346. A switch (not shown) allows application of electrosurgical power to instead be directed to a distally oriented conductive surface, as described hereinbelow.

Figure 17:
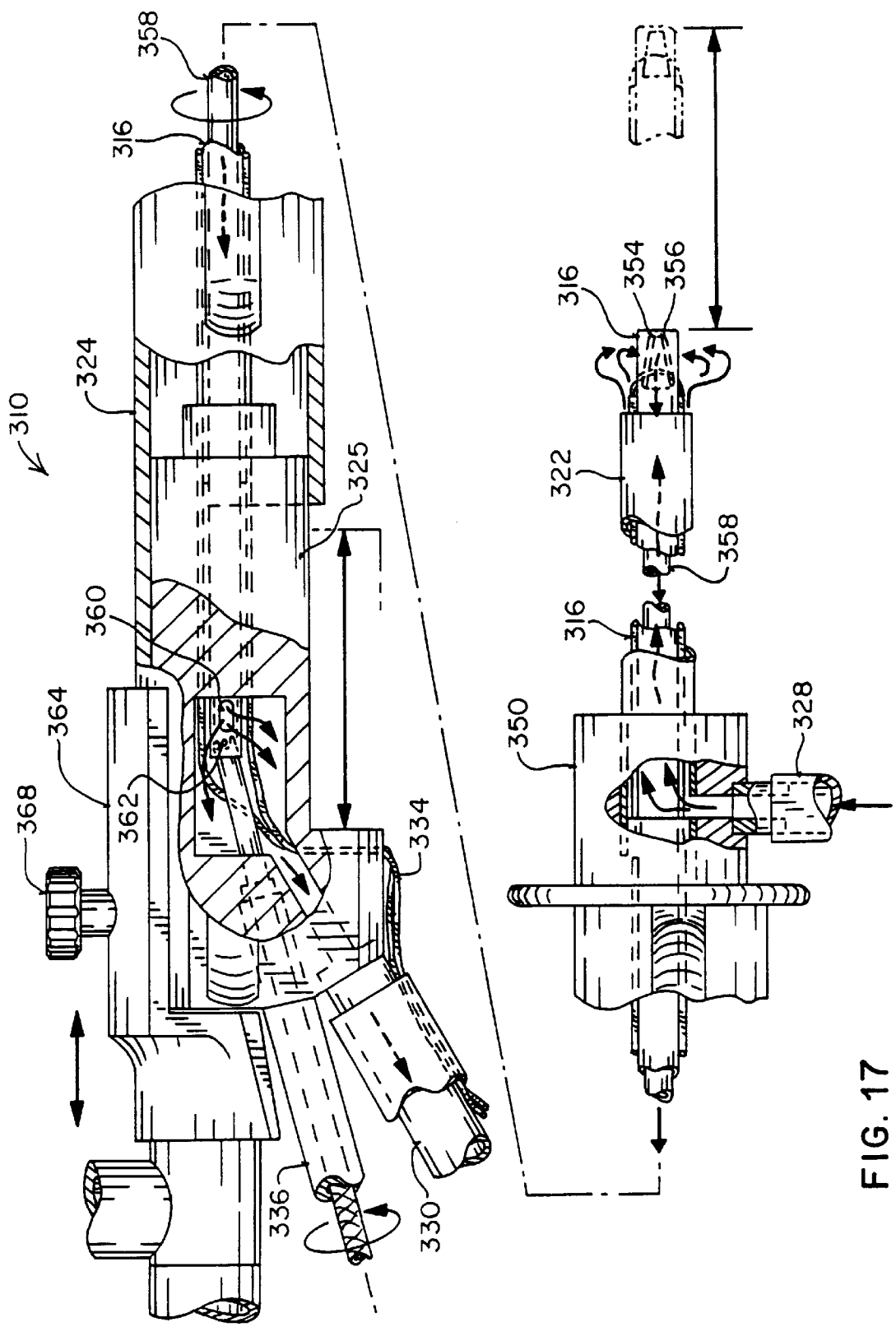
FIG. 17 illustrates the flex drive connection and the aspiration and irrigation flow paths for the probe of FIG. 15.

Referring now to FIG. 17, irrigation fluid supplied to irrigation port 328 enters the probe at a sheath coupler 350, and then flows distally through an infusion lumen of sheath 322. The sheath ends proximally of the distal end of shaft 316 so that the irrigation fluid flows outward into the body cavity, generally washing distally over the scope 320 and cutting member 318. The aspiration flow path enters shaft 316 at an aperture 354, also entering a shaving aperture 356 near the distal end of a chopping tube 358. Chopping tube 358 rotates within shaft 316 so that aperture 354 and shaving port 356 shear tissue fragments from the strips which are directed into aperture 354.

The aspiration flow path exits chopping tube 358 at a proximal flow port 360, and flows into an internal cavity of disposable cartridge 325. Flex drive input 336 rotates the chopping tube by means of a drive pin 362. The drive shaft, connector wires, and aspiration hose reciprocate with disposable cartridge 325 and shaft 316, and flex easily to allow manipulation of the probe. An optical image eyepiece adapter 364 is removably mounted to proximal housing 324 with a thumbscrew 368. Optical adapter 364 typically allows connection of an illumination source, video cameras for viewing and/or recording of the resection procedure, and the like. Optionally, a dedicated pressure sensing lumen may extend between the proximal and distal ends of the probe to accurately measure uterine distension fluid pressure at the proximal handle.

Figure 18:
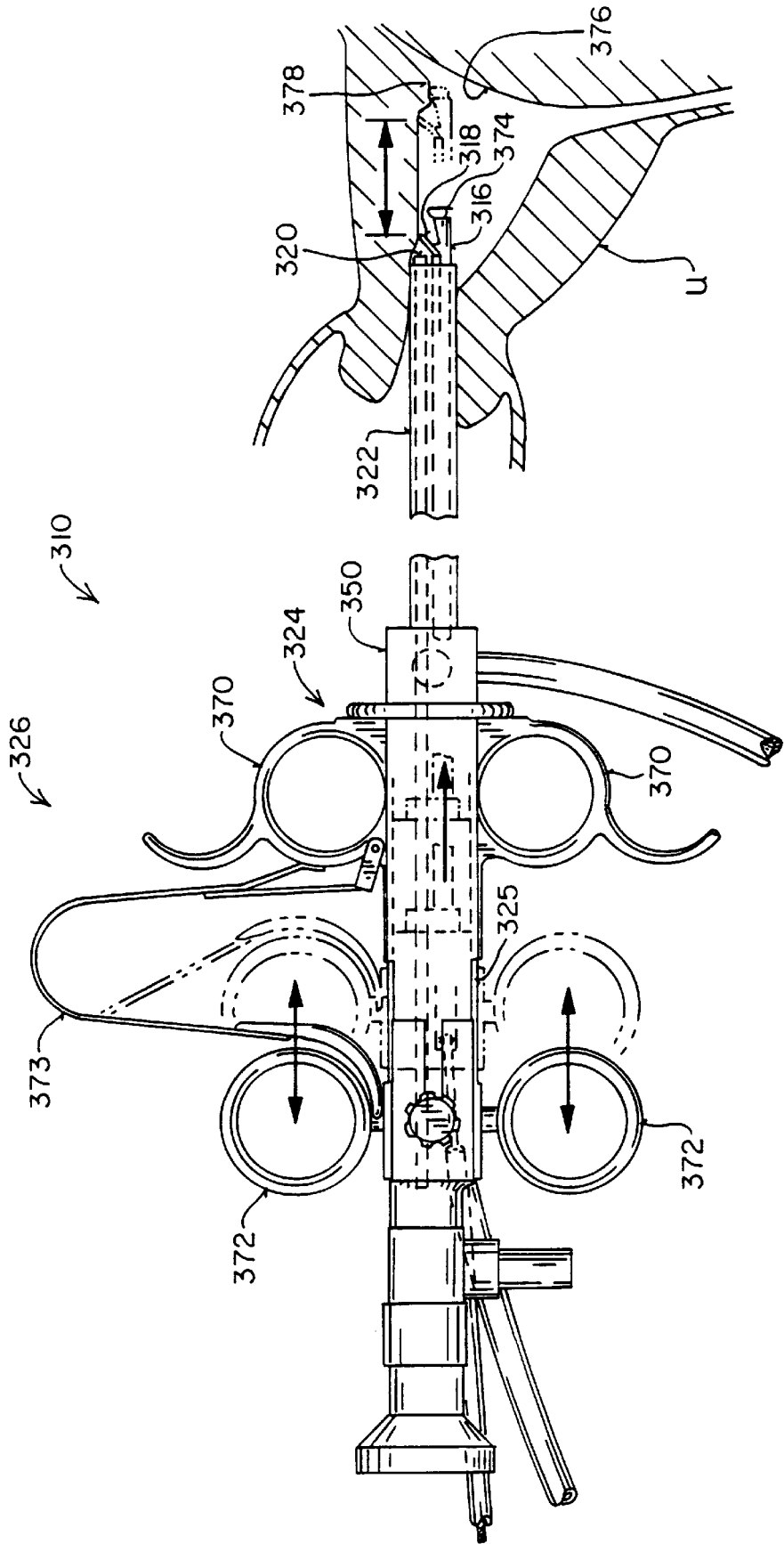
FIG. 18 illustrates a method of use of the probe of FIG. 15 for trans-cervical fibroid removal from the uterus.

Referring to FIG. 18, an exemplary method for using resection probe 310 typically comprises transcervically introducing sheath 322 into the uterus U. Such insertion is facilitated by use of an obturator. Sheath 322 is preferably rigid, ideally comprising a composite insulating material such as fiberglass or the like. Manipulation of the probe is facilitated by limiting the sheath to a maximum of about 327 Fr (about 9 mm in diameter). Once the sheath is properly positioned, the obturator is removed and the shaft 316, cutting member 318, and the scope 320 are inserted through the shaft and proximal housing 324 is attached to sheath coupling 350.

The probe is manipulated from the proximal housing 324 using articulation handle 326. The surgeon inserts the fingers of one hand through finger handle 370 and inserts the thumb of the same hand through thumb ring 372. Preferably, the fingers are held stationary while the thumb ring extends the shaft and cutting member distally from the sheath. Thumb ring 372 is biased toward the proximal direction, so that removal of strips of tissue actually take place under the assistance of biasing spring 373.

Removal of fibroid tissue from the uterus U begins with the cutting member 318 extended distally from the sheath 322. As illustrated in FIG. 18, the shaft is generally aligned with the tissue to be removed so that proximally actuating thumb ring 372 draws cutting member 318 through the fibroid tissue. The procedure is directed using scope 320, preferably while the scope and sheath are held substantially motionless using finger handle 370. Performing each cut towards the viewing optics helps to avoid inadvertently perforating uterus U, the cutting member defining a maximum depth of the cut. However, proximally oriented tissues 376 cannot easily be cut by such a proximal translation, while limiting the direction of the cut also limits the ability of the probe to remove axially oriented tissue 378 which is near the far end of the cavity.

To allow probe 310 to provide therapy for substantially all fibroid tissues in uterus U, the distal end of shaft 316 includes a distally oriented electrically conductive surface 374. Conductive surface 374 is energized by the same electrosurgical power unit as is used for cutting member 318. Preferably a switch allows selection of either one the other electrosurgical surfaces. Conductive surface 374 is swept back and forth over proximally oriented fibroid tissue 376 and adjacent axially oriented tissue 378, ablating these tissues without cutting or puncturing the wall of the uterus.

In an alternative embodiment of the present method, the surgeon may manipulate the thumb ring relative to the finger handle to bring the cutting member 318 to a preferred distance from scope 320, at which the scope provides the optimum field of view. The thumb and fingers are then held fixed relative to each other, and the shaft and housing assemblies are withdrawn proximally from the body cavity. This provides a longer cutting stroke for cutting member 318, and decreases the time required for the resection procedure, particularly when removing tissue from the uterus which is generally axially longer than a single stroke of the handle.

Figures 19, 19A:
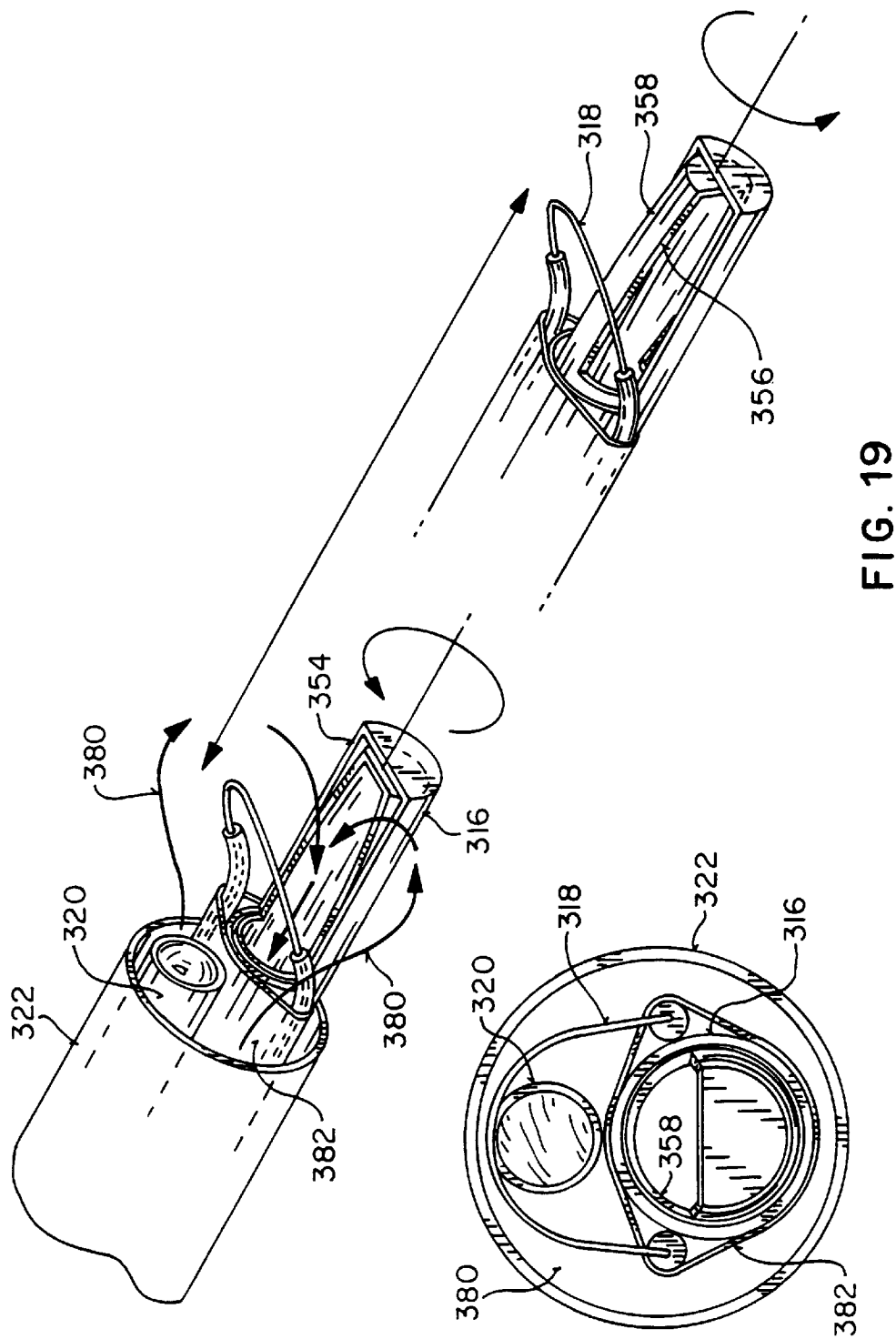
FIGS. 19 and 19A illustrate the axial cutting motion of the cutting member and chopping mechanism, and also show the irrigation and aspiration fluid flow paths at the distal end of the probe of FIG. 15.
Figure 24:
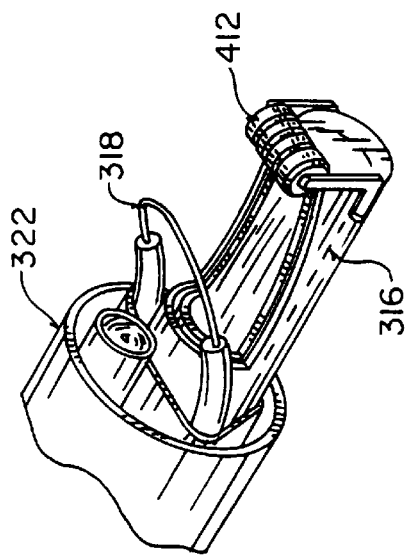
FIGS. 24 through 27 illustrate distally oriented electrically conductive surfaces for use with the probe of FIG. 15.
Figure 25:
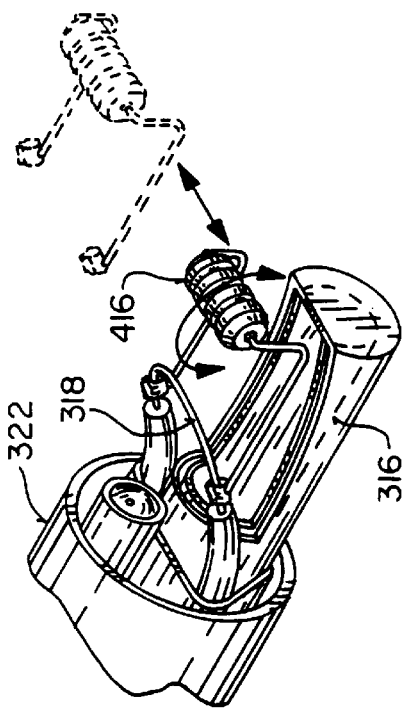

Referring now to FIG. 19, the orientation and flow of aspiration flow path 380 over the imaging fiber-optics 320 is illustrated. In the exemplary embodiment, the proximal ends of cutting member 318 are disposed within insulated tubes which are soldered to shaft 316, the tubes and shaft being insulated with shrink-wrap tubing 382. Optionally, the shrink-wrap tubing extends distally onto the angled portion of cutting member 318 to direct the irrigation fluid flow 380 toward the tissue being cut. Regardless, the use of aspiration flow path to direct the strips of tissue into aperture 354 of shaft 316 leaves the distal end of the shaft with no protruding structure to interfere with the depth of tissue being cut, or to obscure the view beyond the distal end of the shaft. The interaction of shaving port 356 on chopping tube 358 with the aperture 354 of shaft 316 is also clearly seen. An end view of these features is shown in FIG. 19A.

FIGS. 20A and 20B illustrate an alternative cutting member 384 having a reduced diameter cutting lobe 386. As can be understood with reference to FIG. 19A, it has been discovered that the cutting member is capable of cutting strips of fibroid tissue which are larger than are easily accommodated by aperture 354 on shaft 316. Reducing the lobe size facilitates the chopping of the strip of tissue and evacuation of tissue from the surgical site. However, reduced diameter lobe 386 also decreases the amount of tissue removed with each pass of cutting member 318, and therefore prolongs the surgical procedure.

FIGS. 21A and 21B illustrate a still further alternative cutting member 388 having a loop 390 which defines a loop lobe and a second lobe 392. Each of these two lobes cuts a separate strip of tissue when alternative cutting member 388 is passed through tissue. These two smaller strips of tissue are more easily accommodated by aperture 354 and therefore increase the speed of tissue removal.

As illustrated in FIGS. 22A and 22B, still further alternative cutting members are possible. Squared cutting member 394 includes a squared loop 396. Three-lobed cutting member 398 includes a central loop 400. It should be appreciated that more than three lobes may also be used, within the scope of the present invention. In general, rounded corners 402 increase the total amount of tissue which can be removed by a cutting member which must fit within a round shroud, as seen in FIG. 19A. Finally, it will be understood that a variety of angles may be used between the cutting member and the probe shaft. Advantageously, a right angle cutting member as illustrated in FIGS. 21A and 21B is in a single focal plane as viewed from the fiber-optic image lens, and therefore helps to ensure accurate optical direction of the resection procedure.

Figure 26:
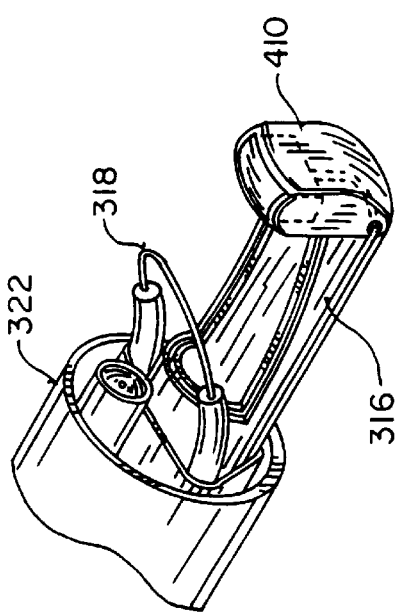
Figure 27:
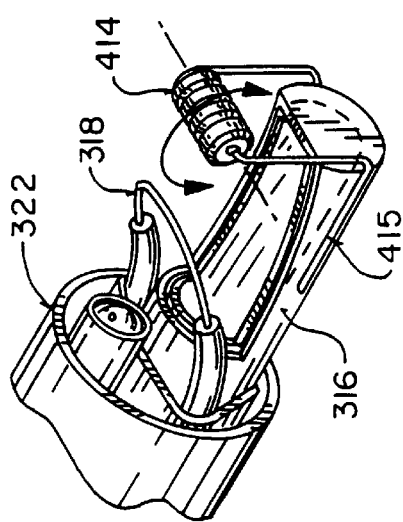

Alternative electrically conductive distal surfaces are illustrated in FIGS. 24–27. A rounded conductive surface 410 facilitates sweeping of the distal end of the shaft 316 over proximally oriented tissues to ablate tissues which are not easily accessible to cutting member 318. Rounded conductive surface 410 also extends upward into the fiberoptic imaging field of view, and may be used to cauterize blood vessels left bleeding by cutting member 318. However, the electrically conductive surface should not protrude upwards so far as to interfere with the cutting depth of cutting member 318. In some embodiments, upward protruding electrically conductive surfaces may be resiliently mounted, for example, on the distal end of a spring wire 415 as shown in FIG. 26, allowing the electrically conductive surface to flex out of the way, thereby avoiding interference with the depth of cut.

Ablation of tissue may be further facilitated by forming the electrically conductive surface as a roller. Such a roller may be located adjacent to the shaft 412, or may alternatively comprise a raised roller 414. To avoid interfering with the depth of tissue resection, a detachable raised roller 416 might be mounted on cutting member 318 by removing the shaft and cutting member through sheath 322. This allows the electrosurgical wires which supply power to the cutting member to also power the ablation or coagulation processes using the electrically conductive surface. Alternatively, the electrically conductive surface may be mounted on the shaft 316 and may be powered by energizing shaft 316 with the proper electrosurgical current. In some embodiments, the distal end of shaft 316 itself forms the electrically conductive surface. Clearly, it is also possible to provide separate electrical lead wires.

As described above, the resection devices and methods of the present invention generally allow removal and evacuation of uterine tissue by applying electrical current at relatively high voltage settings through a surgical instrument. The heat generated from the resistance of tissue to the flow of electrical current "vaporizes" the adjacent cells and also cauterizes small blood vessels. The present invention further provides tissue removal methods and devices which promote vaporization of a substantial portion of the target tissue to be removed, preferably vaporizing the majority of the target tissue, and in some cases vaporizing substantially the entire target tissue.

In tissue vaporization, the heat from the electrocautery current causes intracellular water to boil, exploding the cells and causing the tissue to apparently melt away. However, a good deal of fine solid debris is created during vaporization, and tissue fragments of various sizes may also be severed and released. This solid debris would significantly degrade the image quality if allowed to accumulate at the surgical site, as described above. Hence, the aspiration of the debris of all forms, simultaneously with the removal of the tissue, substantially improves the quality of the image of the tissue removal procedure which is available, regardless of the relative amount of tissue which is vaporized relative to the amount which is released as strips, morsels, or fragments.

Figure 28:
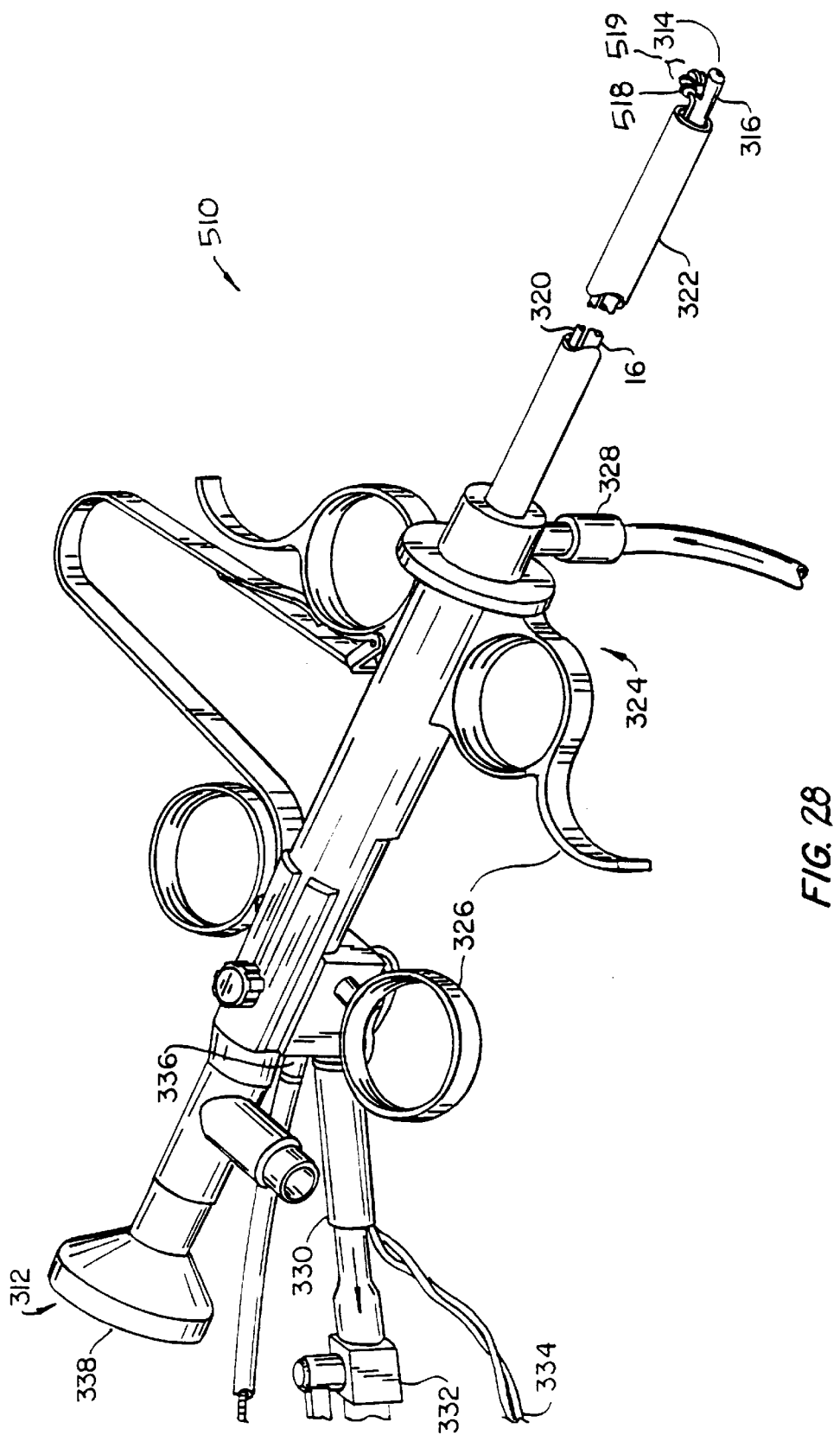
FIG. 28 is a perspective view of yet another probe according to the principles of the present invention, showing a plurality of rolling elements to enhance tissue removal.

For the above reasons, the embodiments of the present invention which emphasize tissue vaporization have structures and methods of use which are similar to those described above. As seen in FIG. 28, a tissue removal probe 510 generally includes proximal end 312 and distal end 314 as described above. Probe shaft 316 supports a vaporizing member 518 near its distal end, the vaporizing member here including a plurality of rolling elements 519. Imaging scope 320 is distally oriented toward vaporizing member 518, and runs proximally within sheath 322.

A probe handle housing 324 includes an actuation handle 326 for axially translating the shaft and vaporizing member relative to the sheath. An irrigation fluid port 328 and aspiration port 330 provide a continuous flow path for a clear, non-conductive fluid such as sorbitol-mannitol, mannitol, glycine, or the like. Alternatively, a conductive fluid might be used, as more fully described in U.S. patent application Ser. No. 08/678,412, filed Jul. 2, 1996, the full disclosure of which is incorporated herein by reference. Aspiration flow is controlled by an aspiration valve 332, so that the distension pressure may be maintained independently from flow. Electrosurgical connector wires 334 and a flex drive input 336 provide external electrical and mechanical power, minimizing the weight of housing 324. An optical image eyepiece 338 is removably attached to housing 324 to optically direct the tissue removal procedure. Optionally, an ultrasound transceiver may be mounted on the distal end of the probe. Such a distal ultrasound transducer may optionally comprise a one- or two-dimensional phased array to allow scanning of the tissue independent of any mechanical movement of the transducer probe.

In the exemplary embodiment, aspiration, mechanical rotation, and electrosurgical potential are coupled to the shaft through a disposable cartridge 325 on shaft housing 324, the disposable cartridge reciprocating with the shaft as shown. This disposable cartridge structure facilitates replacement of the vaporizing member/shaft assembly (including the inner and outer tubes of the chopping mechanism or "morcellator") which would otherwise limit probe life. Fluid which leaves aspiration port 330 is directed through a filter canister 342 and then to an aspiration sump 344. Filter 342 removes the solid tissue fragments from the aspiration fluid for analysis. Sump 344 is preferably connected to a standard vacuum supply line to promote the withdrawal of aspiration fluid through the probe. Aspiration vacuum control is conveniently provided by aspiration valve 332 (see FIG. 28).

Mechanical power is supplied to flex drive input 336 by drive motor 348. Drive motor 348 preferably rotates at least in the range between 500 and 1500 rpm, and typically allows for rotation in either direction, or oscillating rotation back and forth. The morcellator generally shears tissue mechanically, without requiring electrosurgical potential.

The morcellator is a preferred feature, to promote aspiration of larger tissue fragments without clogging, but may not be required where the tissue is substantially entirely vaporized, or where tissue fragment size is limited by the shape of the rolling element of the vaporizing member, the electrosurgical power supplied, the relative motion of the rolling elements against the target tissue, and the like. Controlled electrosurgical power is supplied through electrosurgical wires 334 to the vaporizing member by power unit 346. A switch (not shown) optionally allows application of electrosurgical power to be directed to an ablation roller mounted distally of the aperture (not shown). Typically, electrosurgical power levels of between about 100 and 250 watts will be provided to effect tissue vaporization. The irrigation and aspiration flow paths, together with the optical viewing scope, are more fully described in co-pending U.S. patent application Ser. No. 08/542,289, the full disclosure of which is herein incorporated by reference.

Figure 29:
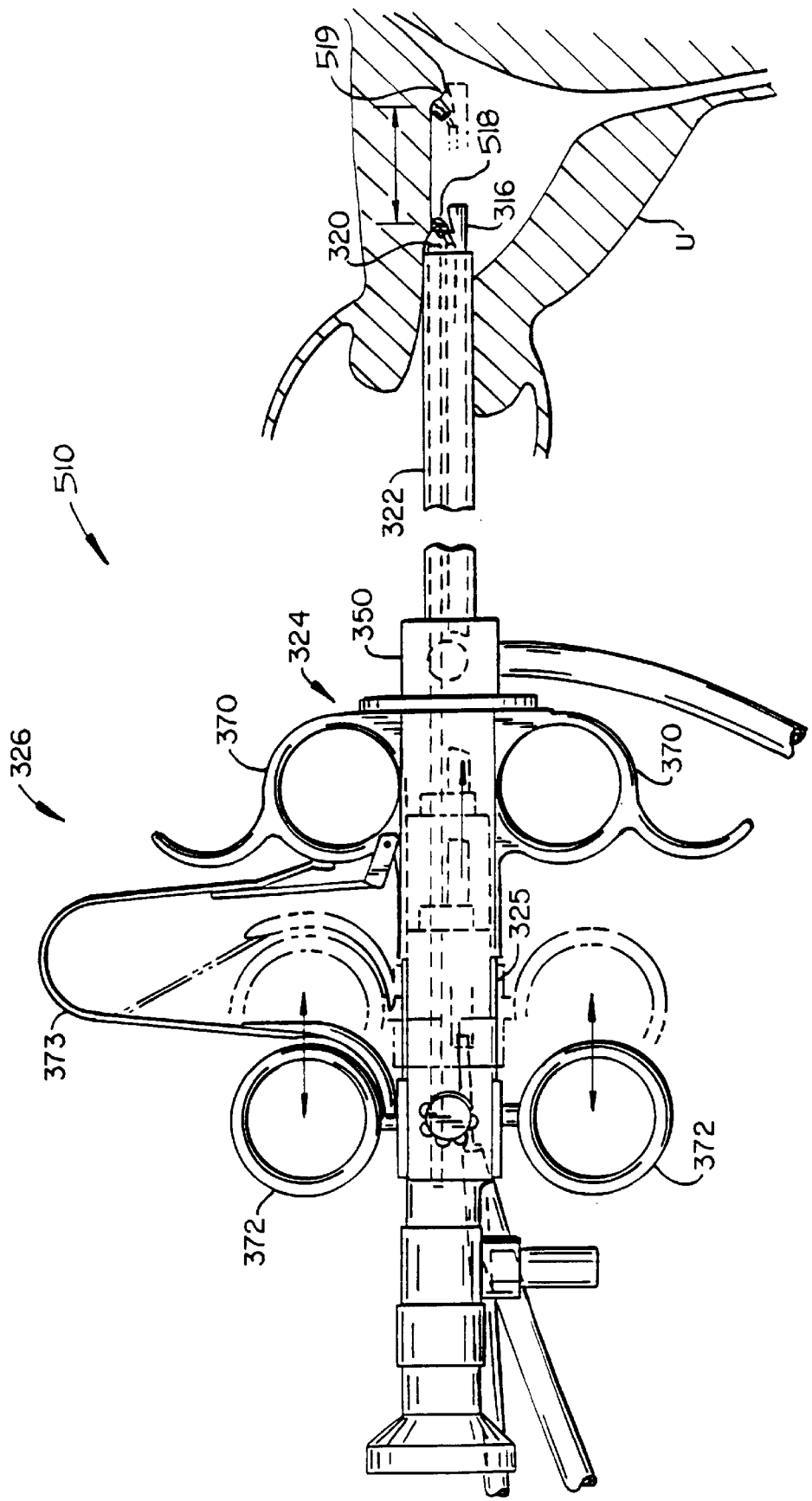
FIG. 29 illustrates a method of use of the probe of FIG. 28 for transcervical fibroid removal from the uterus.

Referring to FIG. 29, an exemplary method for using tissue removal probe 510 typically comprises transcervically introducing sheath 322 into the uterus U. Such insertion is facilitated by use of an obturator, as described above.

Manipulation of the probe is facilitated by limiting the sheath to a maximum of about 27 Fr (about 9 mm in diameter). Once the sheath is properly positioned, the obturator is removed and the shaft 316, vaporizing member 518, and the scope 320 are inserted through the shaft and proximal housing 324 is attached to sheath coupling 350.

The probe is manipulated from the proximal housing 324 using articulation handle 326. The surgeon inserts the fingers of one hand through finger handle 370, and inserts the thumb of the same hand through thumb ring 372. Preferably, the fingers are held stationary while the thumb ring extends the shaft and cutting member distally from the sheath. Thumb ring 372 is biased toward the proximal direction, so that removal of strips of tissue typically takes place under the assistance of biasing spring 373.

Removal of fibroid tissue from the uterus U begins with the vaporizing member 518 extended distally from the sheath 322 and energized with electrocautery potential, as described above. As illustrated in FIG. 29, the shaft is generally aligned with the tissue to be removed so that proximally actuating thumb ring 372 draws vaporizing member 518 through fibroid and/or endometrial tissue. The procedure is directed using scope 320, preferably while the scope and sheath are held substantially motionless using finger handle 370. Performing each cut towards the viewing scope helps to avoid inadvertently perforating uterus U.

In an alternative embodiment of the method of the present invention, the surgeon may manipulate the thumb ring relative to the finger handle to bring vaporizing member 518 to a preferred viewing distance from scope 320, and then translate the shaft and housing assemblies together proximally. This provides a longer cutting stroke for vaporizing member 518, and decreases the time required for the tissue removal procedure.

As vaporizing member 518 moves proximally, rolling elements 519 distribute the electrosurgical potential over a greater frontal area than wire 521 otherwise would alone. The disks generally have outward radial edges which concentrate the radio frequency at discrete intervals along the frontal area, and the disks will generally roll against (and thereby maintain continuous contact with) unvaporized fibroid or endometrial tissue to enhance vaporization. The edges of the rolling elements are within a predetermined separation distance, ideally being fanned outward radially along the arched wire. Optionally, most or substantially all of the adjacent tissue will be vaporized. Vaporization of substantially the entire removed tissue can generally be provided by electrical current at voltage settings of between about 1,000 and 9,000 volts, typically with an alternating current of between about 500 and 1,000 KHz.

Alternatively, slightly lower electrosurgical potential, a greater separation between rollers, or an increase in cut depth allows discrete tissue fragments to be severed from the uterus by the vaporization of adjacent tissues. Generally, fragmentation will occur with deeper, more aggressive cuts in which roughly similar power settings are used. The predetermined separation distance between rollers generally helps to limit the width of released tissue fragments. Such limited-width tissue fragments are significantly easier to draw into the morcellator for extraction.

Regardless of whether tissue is removed primarily by vaporization or by fragmentation combined with vaporization, the cutting member will preferably have an increased frontal or axial projection area, and can therefore remove a greater volume of tissue with each stroke without overwhelming the morcellator when compared to a cutting wire. In fact, where substantially all the removed tissue is vaporized, no morcellator may be required to evacuate the remaining debris, although the morcellator is generally preferred to avoid clogging. Those of skill in the art will appreciate that such methods and devices will have many advantageous applications, including for the removal of selected thoracic tissues, particularly lung tissue, tissues of the bladder, and tissues of the prostate.

Referring now to FIGS. 30 and 31, the orientation and flow of aspiration flow path 380 over scope 320 is illustrated. The interaction of shaving port 356 on chopping tube 358 with aperture 354 of shaft 316 is also clearly seen. In the exemplary embodiment, vaporizing member 518 includes an energized wire 521 having proximal ends disposed within and electrically insulated from support insulated tubes 581 which are soldered to shaft 316, the tubes and shaft being insulated with shrink-wrap tubing 382. As shown most clearly in the simplified end view of FIG. 31, wire 521 forms a transverse arch along which the rolling elements 519 are disposed. Insulation 583 between wire 521 and tubes 581 is also shown. Preferably, the entire vaporizing member 518, including wire 521 and rolling elements 519, is smaller than the lumen of sheath 322 to facilitate insertion and removal of the cutting member/shaft assembly.

Referring now to FIGS. 32A and B, rolling element 519 optionally comprises a simple disk with a central passage 590 for the wire. The rolling element generally comprises an electrically conductive material which will withstand the temperatures created in the ablation process, preferably comprising brass, stainless steel, plated steel, or plated stainless steel.

Referring to FIGS. 33–33B, a plurality of spurred rolling elements 592 optionally directly replace the plurality of disks in cutting member 318 (see FIGS. 11 and 12). Each spurred rolling element includes a plurality of radially protruding elements 594 which enhance tissue/rolling element friction to promote rolling, and which also further direct vaporizing energy into the fibroid tissue, thereby increasing the volume of tissue removed with each pass. Optionally, the electrosurgical potential applied through such a spurred rolling element may promote removal of tissue through increased vaporization depth, and may also enhance fragmentation and severing of the adjacent unvaporized tissue, increasing the efficiency of tissue removal.

Optionally, a plurality of spurred rolling elements may be fanned outward along a curved wire, as described above. Alternatively, a single spurred cylinder 596 supported on a straight, transverse energized wire could span the ablation area as a single roller to produce a square cut. In a still further alternative, a spurred sphere 598 mounted on a similar straight energized wire will create an arched cut.

Figure 34:
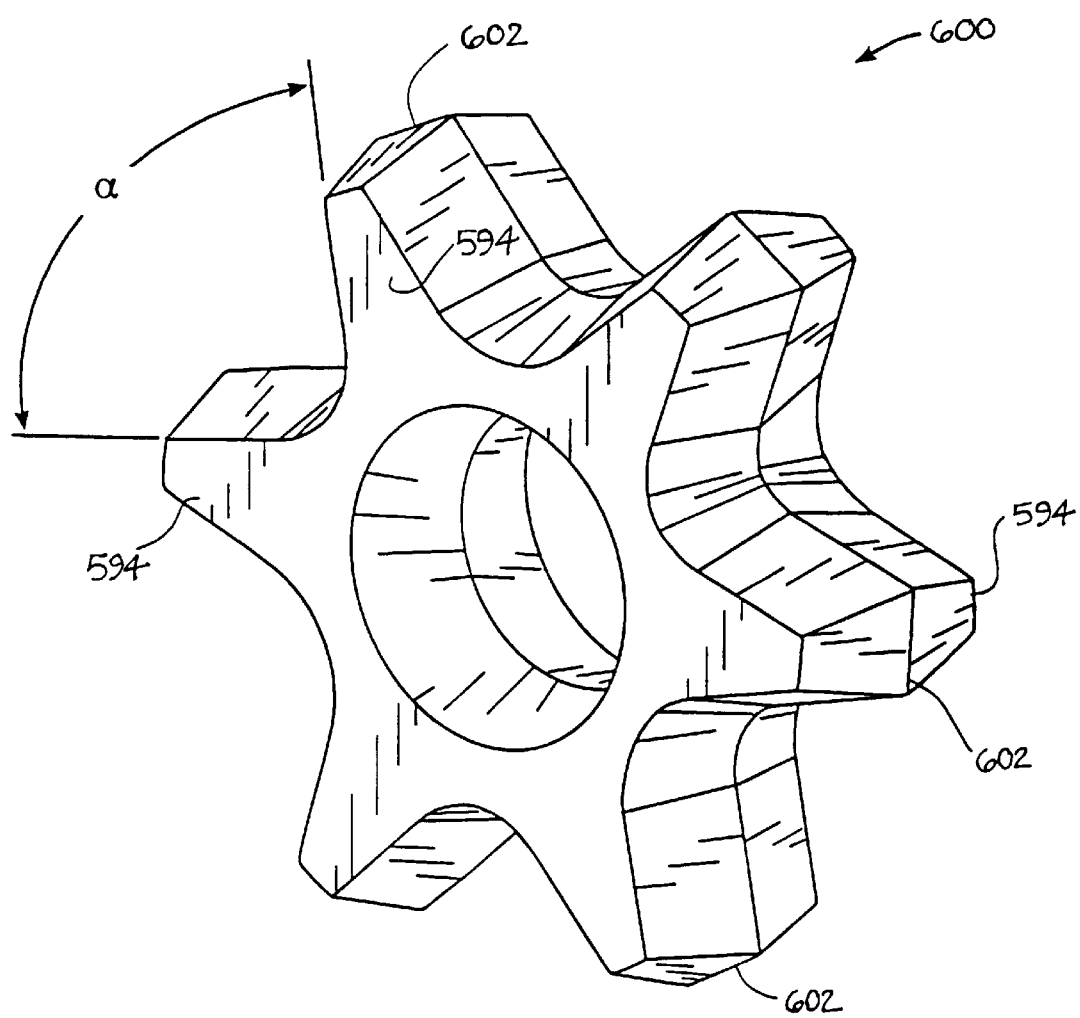
FIG. 34 is a perspective view of an exemplary spurred rolling element for use in the cutting member of the probe of FIG. 28.

Referring now to FIG. 34, an exemplary spurred rolling element 600 will be typically include between 4 and 10 radially protruding elements 594, ideally having about 6. The spurred rollers will generally be between about 0.050 inches and 0.125 inches in diameter (to the ends of protruding elements 594), with an axial thickness of between about 0.005 inches and 0.09 inches. In the exemplary embodiment of the roller, the surfaces between adjacent protruding elements define an angle $\alpha$ of roughly 45°. Preferably, there will be between about 6 and 50 such rollers along the wire of the cutting element.

The ends 602 of protruding elements 594 will ideally slope radially outward toward the axial center, as shown. While the preferred slope of ends 602 will be up to about 20°, it should be understood that the actual shape of the rollers may vary somewhat from the theoretical shape shown. In fact, the rollers will often be fabricated by masking sheets of metal and chemically etching the material surrounding the desired roller shape, generally producing somewhat rounder edges than that shown at the end surface 602 of protruding element 594. The rollers will generally be formed from stainless steel, but may alternatively comprise titanium, tungsten, or the like. optionally, a thin layer of low friction coating such as PTFE may reduce charring and the buildup of electrosurgical debris on roller 602.

Figure 35:
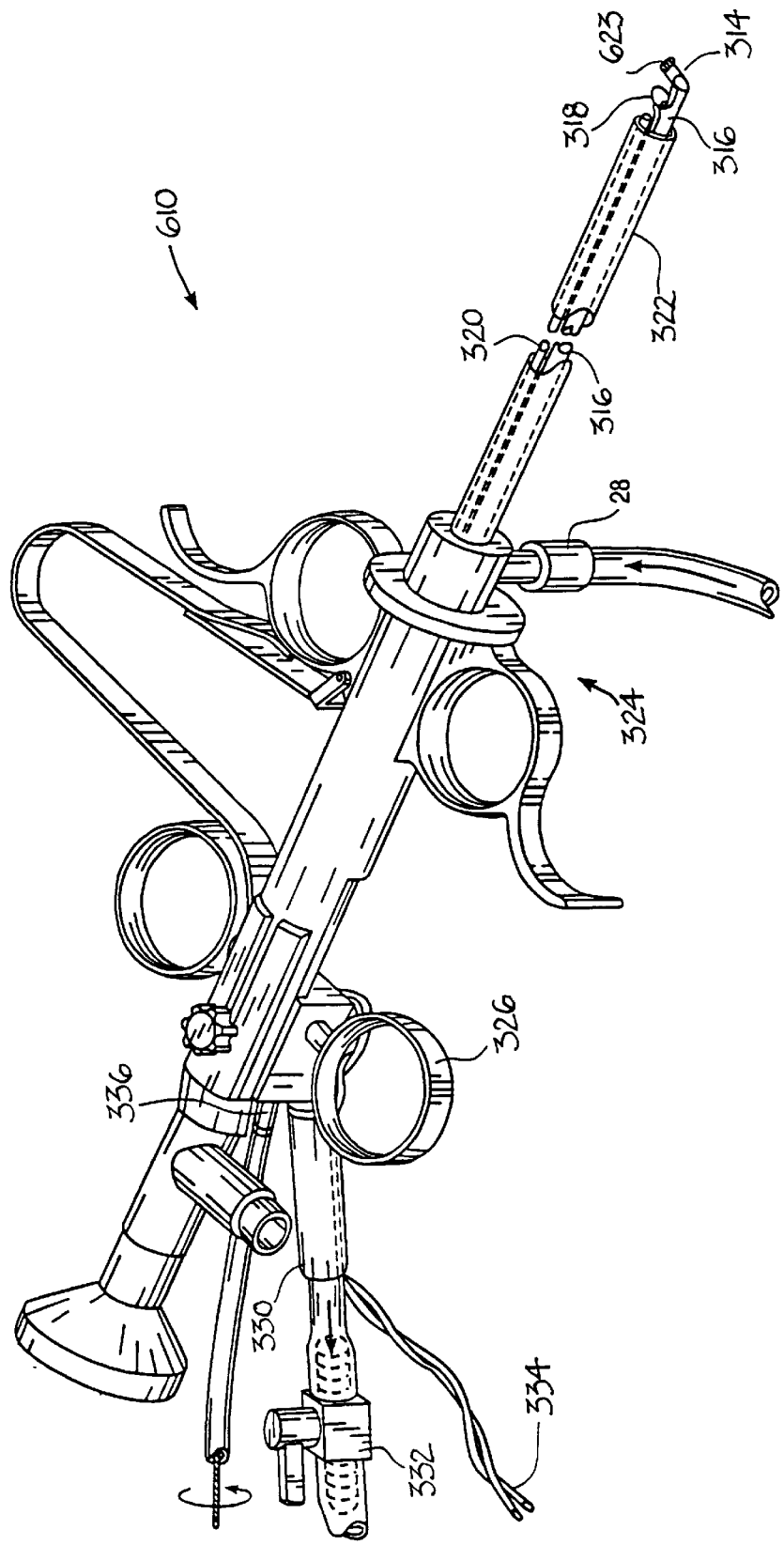
FIG. 35 is a perspective view of yet another resection probe according to the principles of the present invention, showing a resiliently mounted ablation/coagulation roller.

Although the frame endcap of probe 200" (see FIG. 12) provides a relatively open structure for clear distal optical visualization, some portion of the distal field of view may be blocked by this structure. Additionally, the use of separate strokes to first pass the electrosurgical cutting wire through tissue, and to later individually cauterize any blood vessels which remain open with the ablation/coagulation surface, can result in a time consuming procedure when a large number of blood vessels are involved. Furthermore, there is some possible interference between the ablation/coagulation surface and the cutting wire during the separate use of each of these structures. To overcome these potential disadvantages, and referring now to FIG. 35, resection probe 610 generally has a structure similar to that of probe 310 (as illustrated in FIG. 15). Imaging scope 320 is again distally oriented toward cutting member 318, and runs proximally within sheath 322. Scope 320 typically comprises a rod-lens imaging scope, alternatively being a fiber-optic scope. A coagulation/ablation roller 623 is disposed near the distal end 314 of shaft 316.

In the exemplary embodiment, aspiration, mechanical rotation, and electrosurgical potential are again coupled to the shaft through a disposable cartridge 625 on shaft housing 324, the disposable cartridge reciprocating with the shaft as shown. This disposable cartridge structure facilitates replacement of the cutting wire/shaft assembly (including the inner and outer tubes of the chopping mechanism) which would otherwise limit probe life. A switch (not shown) allows application of electrosurgical power to be directed to roller 623. The electrical potential may be conducted distally through shaft 316, or separate wires coupled to the roller may alternatively be provided. Preferably, roller 623 and cutting member 318 may be energized simultaneously, and ideally, using independently variable power. Optionally, an additional separate power supply energizes the roller.

As illustrated, resiliently mounting roller 623 to shaft 316 allows the roller to protrude radially beyond the cutting wire, but also allows the roller to be displaced by pressing the roller out of the way during cutting. In some embodiments of the resection method of the present invention, no energy is supplied to the roller during this tissue removal, hence, the roller is optionally removed or retracted during the cutting stroke, as described hereinbelow.

In an alternative embodiment of the method of the present invention, the surgeon may manipulate the thumb ring relative to the finger handle to bring the cutting member 318 to a preferred viewing distance from scope 320, and then translate the shaft and housing assemblies together proximally. This provides a longer cutting stroke for cutting member 318, and decreases the time required for the resection procedure. Regardless, proximally oriented tissues 676 cannot easily be cut by such a proximal translation, and a proximal cutting direction also limits the ability of the probe to remove axially oriented tissue 678 near the far end of the cavity.

The difficult to reach areas, and any bleeders left open by the cutting wire, are treated by heating the tissue with roller 623 (or with some other ablation electrode shape). Roller 623 applies coagulation electrocautery current to a larger area of tissue than the cutting wire, creating heat which stops bleeding and/or kills endometrium. Roller 623 may be separately energized and rolled over the fundus (top of the uterus), the entrance to the fallopian tube, or other proximally oriented fibroid tissue 676 and adjacent axially oriented tissue 678, ablating these tissues without cutting or puncturing the wall of the uterus.

The roller may also be independently energized after one or more strips of tissue have been severed and aspirated to cauterize any blood vessels which are left bleeding by the cutting wire. During such ablation or coagulation, no energy need be supplied to the cutting member, with the coagulation surface preferably extending radially beyond the cutting wire and into a clear field of view of the scope.

In a still further embodiment of the resection method according to the present invention, the roller and the cutting member may be simultaneously energized during the cutting stroke. The roller is aligned with the cutting member, and will coagulate any open blood vessels very soon after they are severed, minimizing both the time required for the procedure and the blood loss, and thus also improving image clarity. By aligning the aperture axially between the cutting wire and the roller, severing of tissue, aspiration of the severed tissue, and coagulative heating may be applied simultaneously during each proximal stroke of the probe.

Figure 37:
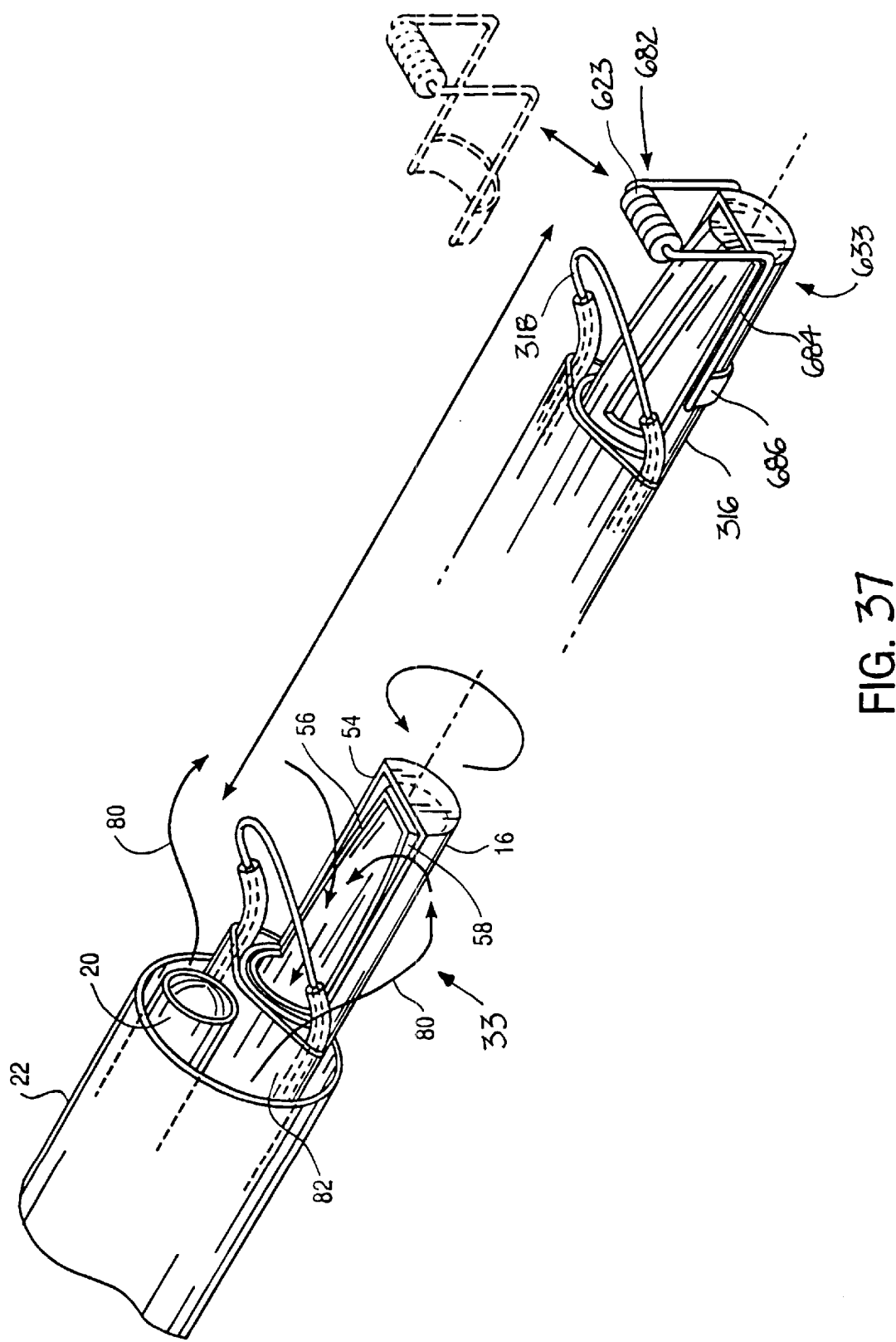
FIGS. 37–37B illustrate alternative removable ablation/coagulation roller clips which removably attach near the distal end of the shaft, for use with the probe of FIG. 35.

Referring now to FIG. 37, the orientation and flow of aspiration flow path 380 over the imaging fiber-optics 320 is illustrated. In the exemplary embodiment, the proximal ends of cutting member 318 are disposed within and electrically insulated from support tubes which are soldered to shaft 316, the tubes and shaft being insulated with shrink-wrap tubing 382.

Figure 36:
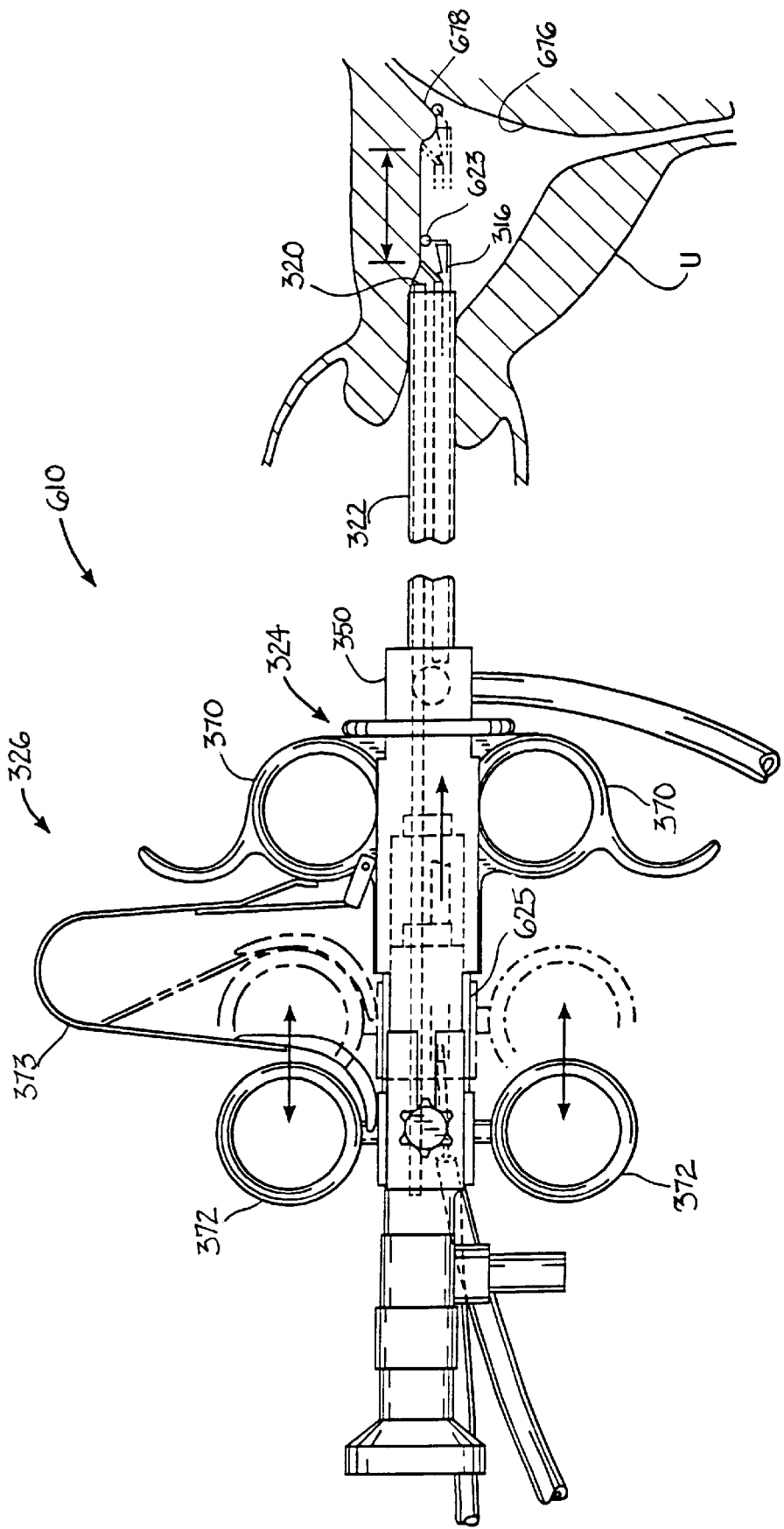
FIG. 36 illustrates a method of use of the probe of FIG. 35 for transcervical fibroid removal from the uterus.
Figure 38:
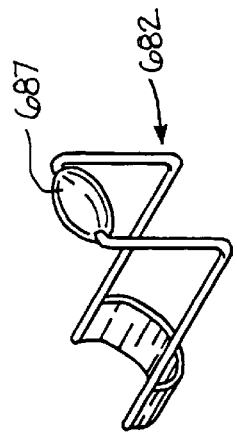
FIG. 38 illustrates an alternative removable ablation/coagulation roller clip for use with the probe of FIG. 37.

In the embodiment of FIG. 37, roller 623 is removably mounted on shaft 316 with a mounting clip 633. Resilient arms 684 allow radial movement of the roller axis (see FIG. 36), while collar 686 removably holds the roller in place, optionally coupling the roller to shaft 316 to provide electrical potential. Such a clip-on ablation roller avoids the need for a second specialized disposable cutter for treatment of proximally oriented surfaces. Several inexpensive rollers of different shapes could be used for more flexible and complete treatment, such as ball 387 shown in FIG. 38.

Figure 37A:
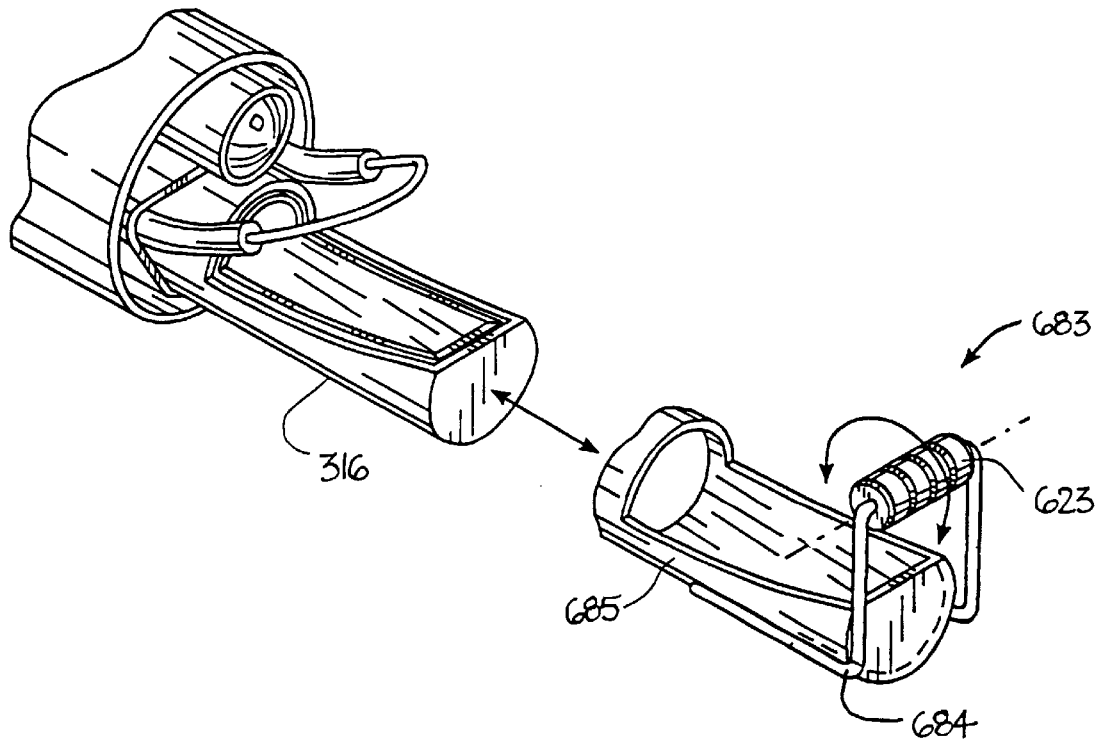
Figure 37B:
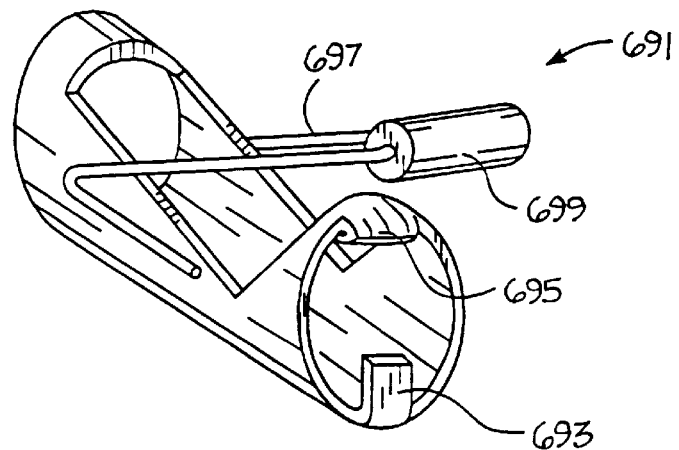

Referring now to FIGS. 37A and B, an alternative mounting clip 683 comprises a closed end tube 685 having an aperture which is at least as large as the aspiration aperture on shaft 316. Closed end tube 685 slides over the distal end of shaft 316 with a friction fit, the closed end ensuring proper axial alignment with the shaft. Arms 684 supporting roller 623 are affixed to the outer surface of the closed end tube.

A preferred mounting clip 691 is formed from tubing which slides over the end of the shaft with a friction fit, a stop tab 693 ensuring axial alignment. Preferred clip 691 also has an upper tab folded over roughly 180° to form a rotational alignment key 695. This key mates with the shape of material removed from the end of the shaft to ensure rotational alignment of preferred clip 691 with the shaft of the probe. Resilient angled arms 697 allow deflection of the roller axis. Here, an optional smooth roller 699 is shown with no grooves.

The ability to snap mounting clip 691 on and off the tip of the cutting member/shaft assembly allows removal of the bulk of the endometrium/myometrium prior to attachment of, and thus without interference from, the coagulation surface. As required, the cutting member/shaft assembly is removed from the uterus through the sheath, and the desired ablation ball or roller clipped onto the distal end. The probe is then reinserted through the sheath, and the attached roller may be used to stop bleeders, to treat the top of the uterus, and to touch up areas which have been missed by the wire. The surgeon can thus alternate between the wire alone and various rollers as appropriate for the individual procedure.

Figure 39:
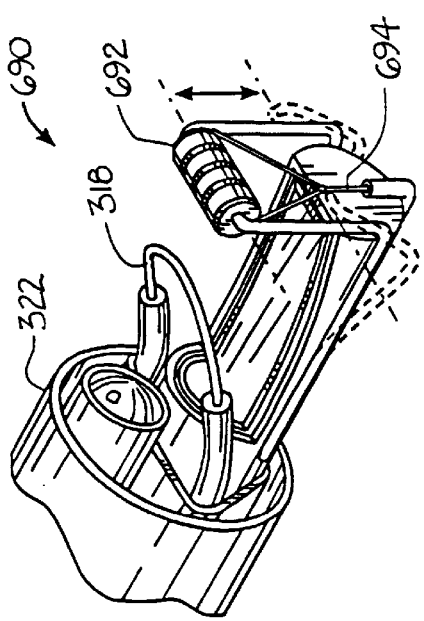
FIG. 39 illustrates a retractable ablation/coagulation roller for use with the probe of FIG. 35.

FIG. 39 illustrates a distal end of a retractable roller probe 690 having a retractable roller 692 which is actuated from the proximal end of the probe using pull wire 694. The roller is again supported on resilient arms which allow the roller's axis of rotation to be displaced toward the axis of the shaft, as shown.

Figure 41:
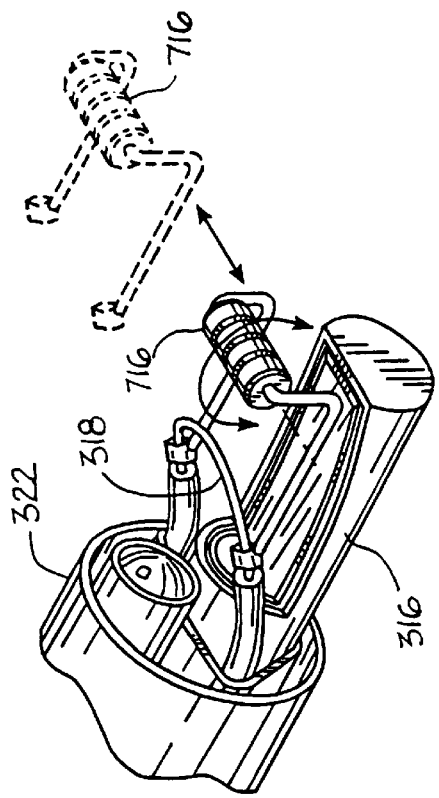
FIG. 41 illustrates a removable coagulation/ablation roller which removably mounts to the cutting wire, for use with the probe of FIG. 35.
Figure 40:
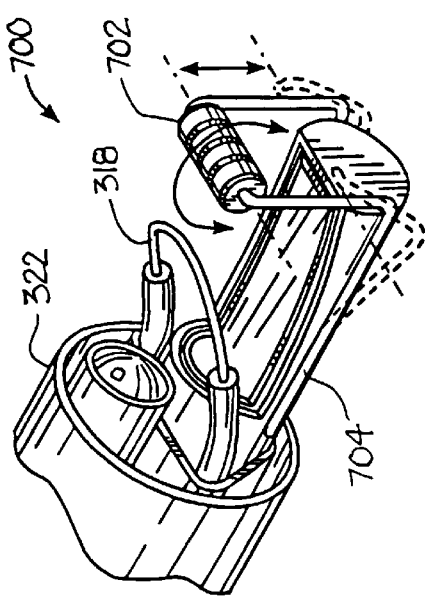
FIG. 40 illustrates a resiliently mounted ablation/coagulation roller for use with the probe of FIG. 35.

Referring now to FIGS. 40 and 41, a resilient roller probe 700 supports resiliently mounted roller 702 on separate electrical lead wires 704. These resilient wires extend proximally along the shaft within the shrink-wrap tubing insulation, optionally also being insulated from shaft 316 within tubes fixed to the shaft, as described above regarding cutting member wires 382. In a still further alternative, detachable roller 716 might be mounted on cutting member 318, also by removing the shaft and cutting member through sheath 322. This allows the electrosurgical wires which supply power to the cutting member to also power the ablation or coagulation processes using the electrically conductive surface.

Although the foregoing invention has been described in detail by way of illustration and example, for purposes of clarity of understanding, it will be obvious that certain changes and modification may be practiced in the scope of the appended claims.

What is claimed is:

1. A method for resecting tissue from the uterus, the method comprising:

removing tissue from the uterus by applying a cutter or radio frequency to the tissue, wherein the tissue is removed in elongate strips;

viewing depth of tissue resection in the uterus while removing the tissue;

chopping the removed strips of tissue into morsels within the uterus; and evacuating the removed tissue from the uterus.

2. A method as claimed in claim 1, wherein the chopping step further comprises shearing the removed tissue between adjacent edges of a chopping mechanism.

3. A method as claimed in claim 2, further comprising rotating one of the adjacent edges.

4. A method for resecting tissue from a uterus, the method comprising:

removing tissue from the uterus by applying a cutter to the tissue, wherein the tissue is removed in elongate strips by manipulating a shaft of a probe to reciprocate an electrosurgical cutting wire of the probe through the tissue adjacent the shaft, the electrosurgical cutting wire protruding radially from the shaft;

viewing depth of tissue resection in the uterus while removing the tissue;

reducing the size of the tissue strips; and evacuating the removed tissue from the uterus.

5. A method for resecting tissue as claimed in claim 4, wherein the electrosurgical cutting wire defines a curve protruding from the shaft, and wherein the reciprocation of the curved wire passes the curve through the tissue so as to remove the elongate strips of tissue.

6. A method for resecting tissue from a surgical site of an internal body cavity, the method comprising:

cutting strips of tissue from the surgical site by axially translating an electrosurgical cutting member of a probe;

aspirating fluid from the surgical site into an aperture on a shaft of the probe so that the strips of tissue enter the aperture; and chopping the strips of tissue into morsels as they enter the aperture and evacuating the morsels through the shaft of the probe.

7. A method as claimed in claim 6, further comprising flowing irrigation fluid over an imaging mechanism and toward the cutting member while optically imaging the tissue and cutting member through the imaging mechanism, and also while cutting the strips of tissue by advancing the cutting member toward the imaging mechanism.

8. A method for resecting tissue from the uterus, the method comprising:

removing tissue from the uterus by applying radio frequency energy to the tissue, wherein the tissue is removed in elongate strips by manipulating a shaft of a probe to reciprocate an electrosurgical cutting wire of the probe through the tissue adjacent the shaft, the electrosurgical cutting wire protruding radially from the shaft;

viewing depth of, tissue resection in the uterus while removing the tissue;

reducing the size of the tissue strips; and evacuating the removed tissue from the uterus.

9. A method for resecting tissue as claimed in claim 8, wherein the electrosurgical cutting wire defines a curve protruding from the shaft, and wherein the reciprocation of the curved wire passes the curve through the tissue so as to remove the elongate strips of tissue.

10. A method for resecting tissue from a patient's internal body structure, comprising:

directing an electrosurgical member of a probe into the tissue by positioning a shaft of the probe adjacent the tissue so that the electrosurgical member protrudes from the shaft into the tissue;

translating the electrosurgical member through the tissue to electrosurgically remove the tissue from the internal body structure;

chopping the removed tissue into smaller morsels; and evacuating the morsels from the patient.

11. The method of claim 10, further comprising ultrasonically measuring the depth of tissue to be removed.

12. The method of claim 10, further comprising optically visualizing the internal body structure while removing the tissue.

13. The method of claim 10, further comprising cauterizing bleeding tissue on the internal body structure.

14. A method for resecting tissue from a patient's internal body structure, comprising:

directing an electrosurgical member of a probe into the tissue by positioning a shaft of the probe adjacent the tissue so that the electrosurgical member protrudes from the shaft into the tissue;

translating the electrosurgical member through the tissue to electrosurgically remove the tissue from the internal body structure;

chopping the removed tissue into smaller morsels; and evacuating the morsels from the patient;

wherein electrosurgical member is a wire, and wherein the wire is translated to remove the tissue in elongate strips.

15. A method for resecting tissue from a patient's internal body structure, comprising:

directing an electrosurgical member of a probe into the tissue by positioning a shaft of the probe adjacent the tissue so that the electrosurgical member protrudes from the shaft into the tissue;

translating the electrosurgical member through the tissue to electrosurgically remove the tissue from the internal body structure;

chopping the removed tissue into smaller morsels by rotating a sharpened blade in the internal body structure to shear the removed tissue between the sharpened blade and an adjacent surface; and evacuating the morsels from the patient.

16. A method for resecting tissue from a body structure, said method comprising:

providing a probe having a proximal end, a distal end, a lumen extending therebetween, and an aperture exposing the lumen near the distal end;

providing an electrosurgical wire near the distal end of the probe, the electrosurgical wire defining a curve protruding from the probe;

providing a drive member rotatably disposed within the probe lumen and having a proximal end and a distal end;

providing a rotatable cutting member at the distal end of the drive member with the cutting member being accessible through the aperture;

positioning said probe at a surgical site near the body structure;

translating the electrosurgical wire along tissue at the surgical site to resect tissue within the curve from the body structure; and rotating the cutting member to chop the removed tissue into smaller morsels.

17. The method of claim 16, further comprising aspirating the morsels from the body structure through the probe lumen.

18. The method of claim 16, further comprising ultrasonically viewing depth of tissue to be removed.

19. A method for resecting tissue from a body structure, said method comprising:

providing a probe having a proximal end, a distal end, a lumen extending therebetween, and an aperture exposing the lumen near the distal end;

providing an electrosurgical wire near the distal end of the probe;

providing a drive member rotatably disposed within the probe lumen and having a proximal end and a distal end;

providing a rotatable cutting member at the distal end of the drive member with the cutting member being accessible through the aperture;

positioning said probe at a surgical site near the body structure;

translating the electrosurgical wire along tissue at the surgical site to resect tissue from the body structure;

rotating the cutting member to chop the removed tissue into smaller morsels; and providing an electrically conductive element on the probe, providing current to the electrically conductive element, and placing the electrically conductive element against bleeding tissue on the body structure to effect cauterization.

20. A method for extracting tissue from a uterus, the method comprising:

removing tissue from the uterus by applying a radio frequency to the tissue with an electrosurgical element of a probe so that a portion of the removed tissue is vaporized;

viewing depth of tissue removed from the uterus while removing the tissue by optically imaging the tissue with a scope of the probe; and evacuating tissue removed from the uterus while removing the tissue by aspirating the removed tissue through an aspiration lumen of the probe;

wherein irrigation fluid flows from adjacent the scope toward the electrosurgical element, and wherein the aspirating step maintains image clarity by drawing removed tissue from adjacent the electrosurgical element away from the scope.

21. A method as claimed in claim 20, wherein a majority of removed tissue is vaporized, and wherein the morcellating step avoids clogging of an aspiration lumen.

22. A method for extracting tissue from a uterus, the method comprising:

removing tissue from the uterus by applying a radio frequency to the tissue with an electrosurgical element of a probe and translating the element through uterine tissue while the element is energized with the radio frequency so that a portion of the removed tissue is vaporized and a portion of uterine tissue is severed;

viewing depth of tissue removed from the uterus while removing the tissue by optically imaging the tissue with a scope of the probe; and evacuating tissue removed from the uterus by morcellating the severed tissue and aspirating the removed tissue through an aspiration lumen of the probe;

wherein irrigation fluid flows from adjacent the scope toward the electrosurgical element, and wherein the aspirating step maintains image clarity by drawing removed tissue from adjacent the electrosurgical element away from the scope.

23. A method as claimed in claim 22, wherein a majority of the removed tissue is vaporized, and wherein the morcellating step avoids clogging of an aspiration lumen.

24. A method for resecting tissue from a surgical site of an internal body cavity comprising:

directing an electrosurgical member of a probe into the tissue by positioning a shaft of the probe adjacent the tissue so that the electrosurgical member protrudes from the shaft into the tissue;

translating the electrosurgical member through the tissue to electrosurgically remove the tissue from the internal body cavity thereby exposing a severed tissue area within the body cavity;

cauterizing the severed tissue area; and evacuating the removed tissue from the body cavity.

* * * * *